(12) United States Patent
Duinat et al.

(10) Patent No.: US 10,052,437 B2
(45) Date of Patent: Aug. 21, 2018

(54) SYRINGE PACKAGING SYSTEM AND SHELL

(71) Applicant: Fresenius Kabi Deutschland GmbH, Bad Homburg (DE)

(72) Inventors: Brigitte Duinat, Grenoble (FR); Tracy Ray Hottovy, Wilson, NC (US); Charles Biancon, Monestier de Clermont (FR); Charles D. Shermer, Raleigh, NC (US); Luc Dorelon, St. Martin de la Cluze (FR)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 15/206,047

(22) Filed: Jul. 8, 2016

(65) Prior Publication Data

US 2017/0007771 A1    Jan. 12, 2017

Related U.S. Application Data

(60) Provisional application No. 62/191,036, filed on Jul. 10, 2015, provisional application No. 62/292,546, filed on Feb. 8, 2016.

(51) Int. Cl.
| | |
|---|---|
| *A61M 5/315* | (2006.01) |
| *A61M 5/50* | (2006.01) |
| *A61M 5/32* | (2006.01) |
| *A61M 5/31* | (2006.01) |
| *A61M 5/00* | (2006.01) |

(52) U.S. Cl.
CPC ........ *A61M 5/31505* (2013.01); *A61M 5/002* (2013.01); *A61M 5/3137* (2013.01);
(Continued)

(58) Field of Classification Search
CPC .......... A61M 5/00; A61M 5/002; A61M 5/31; A61M 5/3137; A61M 5/32; A61M 5/3202;
(Continued)

(56) References Cited

U.S. PATENT DOCUMENTS 3,342,319 A    9/1967  Faulseit
4,979,616 A *  12/1990 Clanton .............. A61M 5/3205
                                                206/364
(Continued)

FOREIGN PATENT DOCUMENTS

WO    WO 2001/023017 A2    4/2001
WO    WO 2006/018626 A1    2/2006

OTHER PUBLICATIONS

European Patent Office, Invitation to Pay Additional Fees and Partial International Search in International Application No. PCT/IB2016/054127 (dated Sep. 27, 2016).
(Continued)

*Primary Examiner* — Bryon Gehman
(74) *Attorney, Agent, or Firm* — Leydig, Voit & Mayer, Ltd.

(57) ABSTRACT

A syringe packaging system including a shell for enclosing a pre-filled syringe is disclosed. The shell includes a first portion having a proximal end and a distal end having a disk-shaped bottom portion; and a second portion having a proximal end and a distal end. With the first portion engaged with the second portion to form the shell, the proximal end of the first portion and the proximal end of the second portion together define a syringe flange having a top wall that defines a shell proximal aperture, a bottom wall, and a sidewall.

35 Claims, 26 Drawing Sheets

(52) U.S. Cl.
CPC ........ *A61M 5/3202* (2013.01); *A61M 5/5086* (2013.01); *A61M 2005/3142* (2013.01); *A61M 2005/31508* (2013.01)

(58) Field of Classification Search
CPC .................. A61M 5/50; A61M 5/5086; A61M 2005/314; A61M 2005/3142; A61M 2005/315; A61M 2005/31505; A61M 2005/31508; A61M 5/31505; A61M 5/31508; B65D 81/02; B65D 85/20
USPC .................................. 206/364, 571
See application file for complete search history.

(56) References Cited

U.S. PATENT DOCUMENTS

| | | | |
|---|---|---|---|
| 5,519,931 A * | 5/1996 | Reich | G21F 5/018 206/365 |
| 5,615,772 A | 4/1997 | Naganuma | |
| 6,073,759 A | 6/2000 | Lalmborne et al. | |
| 6,368,305 B1 * | 4/2002 | Dutton | A61M 5/31501 604/192 |
| 6,929,126 B1 | 8/2005 | Herbert | |
| 9,144,465 B2 * | 9/2015 | Hunkeler | A61M 5/002 |
| 9,333,146 B2 | 5/2016 | Perot et al. | |
| 9,333,288 B2 | 5/2016 | Hilliard et al. | |
| 2011/0087173 A1 | 4/2011 | Sibbitt, Jr. et al. | |
| 2013/0081974 A1 | 4/2013 | Hilliard et al. | |
| 2013/0082057 A1 | 4/2013 | Schiff et al. | |
| 2014/0078854 A1 * | 3/2014 | Head | A61M 5/002 206/364 |

OTHER PUBLICATIONS

European Patent Office, International Search Report in International Application No. PCT/IB2016/054127 (dated Dec. 16, 2016).

European Patent Office, Written Opinion in International Application No. PCT/IB2016/054127 (dated Dec. 16, 2016).

* cited by examiner

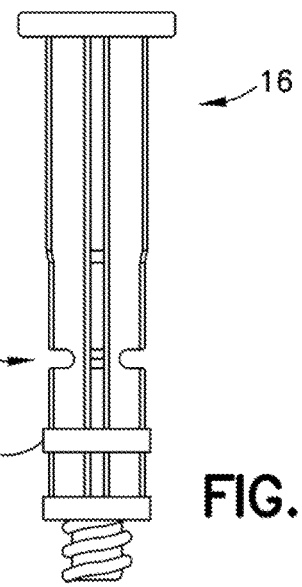
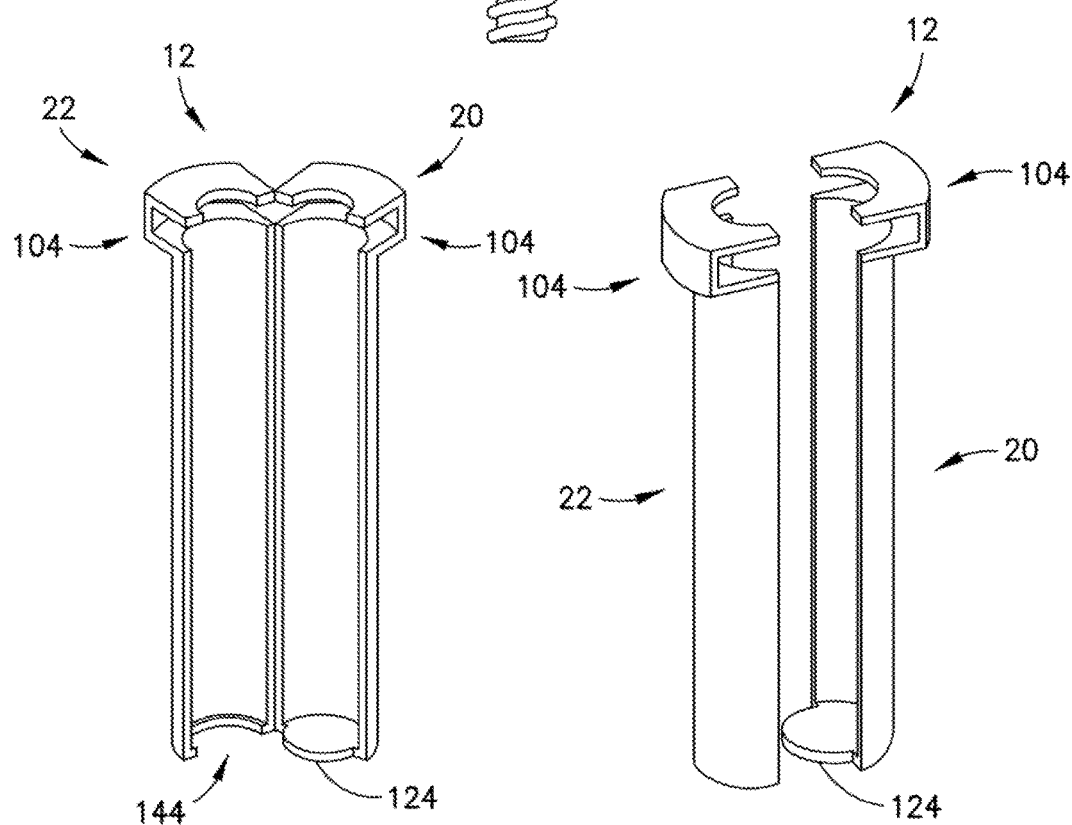
FIG.21
FIG.22
FIG.23

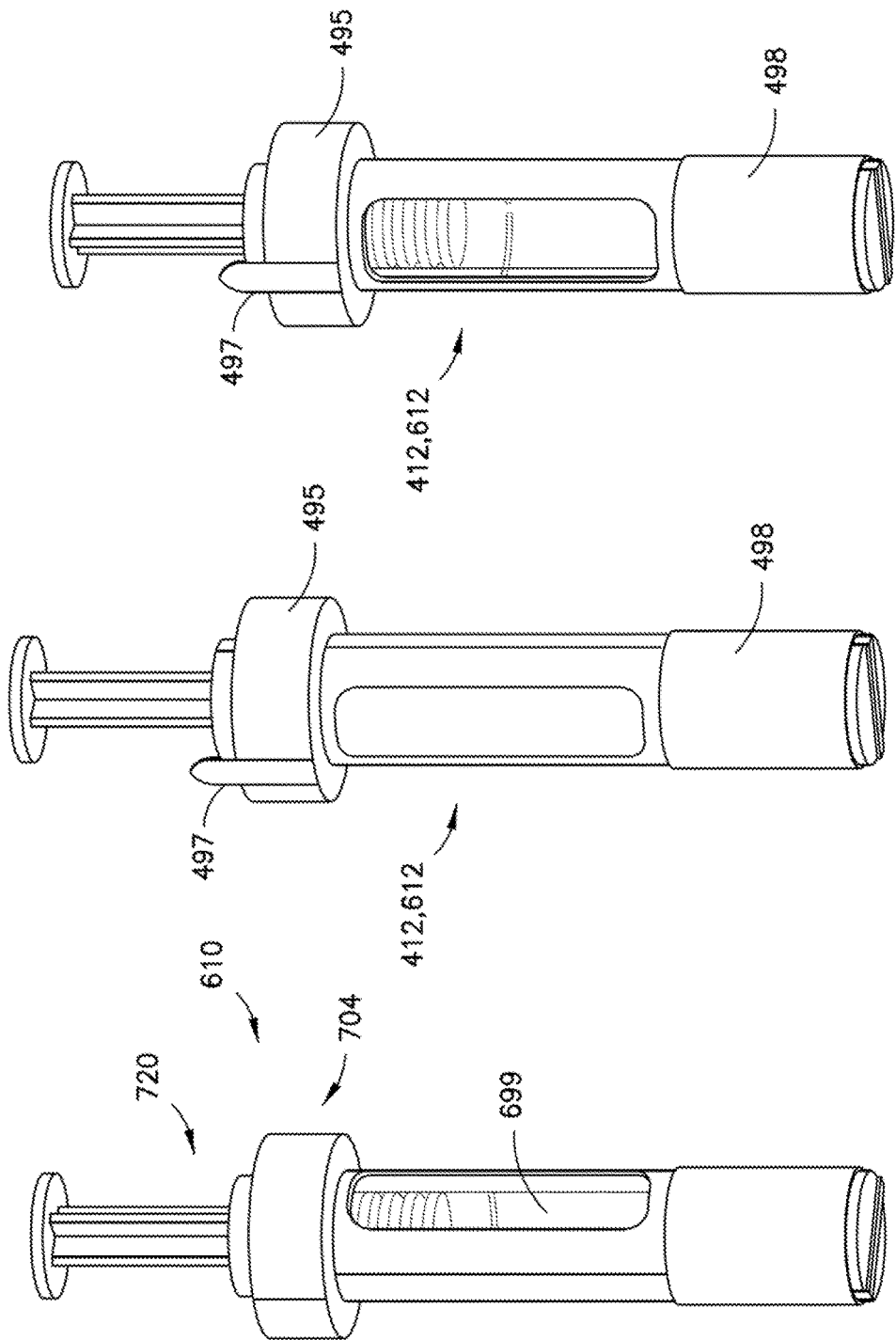

SYRINGE PACKAGING SYSTEM AND SHELL

CROSS-REFERENCE TO RELATED APPLICATIONS

This patent application claims the benefit of U.S. Provisional Application No. 62/191,036, filed Jul. 10, 2015, and U.S. Provisional Application No. 62/292,546, filed Feb. 8, 2016, which are both incorporated herein by reference in their entireties.

BACKGROUND OF THE INVENTION

Field of the Disclosure

The present disclosure relates generally to a syringe assembly adapted for delivery of a fluid. More particularly, the present disclosure relates to a syringe packaging system that allows for reduced storage space of a syringe assembly.

Description of the Related Art

Syringe assemblies, and in particular hypodermic syringes, are well known in the medical field for dispensing fluids, such as medications. A conventional syringe typically includes a syringe barrel with an opening at one end and a plunger mechanism disposed through the opposite end. The plunger mechanism typically includes a plunger rod extending through the barrel, with a plunger head or stopper disposed at the end of the plunger rod within the syringe barrel, and with a finger flange at the other end of the plunger rod extending out of the syringe barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the syringe barrel for attachment with a fluid line of a patient. Upon application of a force to depress the plunger rod and stopper through the syringe barrel towards the front end of the syringe barrel, the contents of the syringe are thereby forced out of the syringe barrel through the opening at the front end for delivery to the patient.

Commonly, hypodermic syringes may be packaged as "pre-filled" devices, wherein the syringe is pre-filled with medication prior to being packaged and delivered to the patient. In this manner, the need for the user to fill the device prior to injection is eliminated, thereby saving time and maintaining consistent volumes for delivery.

However, packaging of such pre-filled syringes tends to be bulky and difficult to ship and store. Pre-filled syringes and pre-filled metered dose syringes are often filled with fluids, such as a medication, at a production facility, packaged, and then shipped to a medical facility. Once at the facility, these syringes are often placed in controlled storage and/or locked cabinets to reduce theft of the syringes themselves and/or of the contents of these syringes. The space within these controlled storage locations is often limited, thus there is a need for a syringe assembly that has a smaller packaging footprint to reduce the amount of storage space required for containing the syringe.

SUMMARY OF THE INVENTION

In accordance with an embodiment of the present invention, a syringe packaging system includes a shell for enclosing a pre-filled syringe. In one embodiment, the shell includes a first shell portion having a proximal end, a distal end, and a first sidewall; a second shell portion having a proximal end, a distal end, and a second sidewall; and a hinge connected to a portion of the first sidewall and a portion of the second sidewall, the hinge connecting the first shell portion and the second shell portion together such that the shell is transitionable between an open position and a closed position in which the syringe barrel is enclosed within the first shell portion and the second shell portion. In another embodiment, the shell includes a first shell portion having a proximal end, a distal end, and a first bottom wall; a second shell portion having a proximal end, a distal end, and a second bottom wall; and a hinge connected to a portion of the first bottom wall and a portion of the second bottom wall, the hinge connecting the first shell portion and the second shell portion together such that the shell is transitionable between an open position and a closed position in which the syringe barrel is enclosed within the first shell portion and the second shell portion.

In accordance with an embodiment of the present invention, a syringe packaging system includes a pre-filled syringe, comprising: a syringe barrel having a proximal end, a distal end, and a sidewall extending therebetween and defining a chamber, the proximal end having a flange; a fluid disposed within the chamber of the syringe barrel; a stopper slidably disposed within the chamber of the syringe barrel; and a plunger rod having a proximal end and a distal end engageable with a portion of the stopper; and a shell enclosing the syringe barrel, the shell comprising: a first shell portion having a proximal end, a distal end, and a first sidewall; a second shell portion having a proximal end, a distal end, and a second sidewall; and a hinge connected to a portion of the first sidewall and a portion of the second sidewall, the hinge connecting the first shell portion and the second shell portion together such that the shell is transitionable between an open position and a closed position in which the syringe barrel is enclosed within the first shell portion and the second shell portion.

In one configuration, with the shell in the closed position, the first shell portion and the second shell portion together define a syringe flange surrounding portion having a top wall that defines a first shell proximal aperture, a bottom wall, and a sidewall extending therebetween, and wherein the syringe flange surrounding portion encloses the flange of the syringe barrel therein. In another configuration, the syringe flange surrounding portion is disposed adjacent the proximal end of the first shell portion and the proximal end of the second shell portion. In yet another configuration, the plunger rod includes a plunger rod disk disposed between the proximal end of the plunger rod and the distal end of the plunger rod. In one configuration, a diameter of the plunger rod disk is greater than a diameter of the plunger rod. In another configuration, with the shell in the closed position, the first shell portion and the second shell portion together define a plunger rod disk surrounding portion having a top wall that defines a second shell proximal aperture, a bottom wall, and a sidewall extending therebetween, and wherein the plunger rod disk surrounding portion encloses the plunger rod disk therein. In yet another configuration, with the shell in the closed position, contact between the plunger rod disk and the plunger rod disk surrounding portion limits movement of the plunger rod in a distal direction and in a proximal direction. In one configuration, with the shell in the closed position, a portion of the plunger rod extends from the second shell proximal aperture. In another configuration, the distal end of the first shell portion includes a first bottom wall and the distal end of the second shell portion includes a second bottom wall, and wherein, with the shell in the closed position, the first bottom wall overlaps the second bottom wall. In yet another configuration, with the shell in the closed position, the overlapping first and second bottom walls shield the distal end of the syringe barrel. In one configuration, one of the first shell portion and the second shell portion include a transparent window. In another configuration, with the shell in the open position, a longitudinal axis of the first shell portion is parallel to a longitudinal axis of the second shell portion.

In accordance with another embodiment of the present invention, a shell for enclosing a pre-filled syringe includes a first shell portion having a proximal end, a distal end, and a first sidewall; a second shell portion having a proximal end, a distal end, and a second sidewall; and a hinge connected to a portion of the first sidewall and a portion of the second sidewall, the hinge connecting the first shell portion and the second shell portion together such that the shell is transitionable between an open position and a closed position, wherein, with the shell in the closed position, the first shell portion and the second shell portion together define a syringe flange surrounding portion having a top wall that defines a first shell proximal aperture, a bottom wall, and a sidewall extending therebetween, wherein, with the shell in the closed position, the first shell portion and the second shell portion together define a plunger rod disk surrounding portion having a top wall that defines a second shell proximal aperture, a bottom wall, and a sidewall extending therebetween, and wherein, with the shell in the open position, a longitudinal axis of the first shell portion is parallel to a longitudinal axis of the second shell portion.

In one configuration, the distal end of the first shell portion includes a first bottom wall and the distal end of the second shell portion includes a second bottom wall, and wherein, with the shell in the closed position, the first bottom wall overlaps the second bottom wall. In another configuration, one of the first shell portion and the second shell portion include a transparent window.

In accordance with another embodiment of the present invention, a syringe packaging system includes a pre-filled syringe, comprising: a syringe barrel having a proximal end, a distal end, and a sidewall extending therebetween and defining a chamber, the proximal end having a flange; a fluid disposed within the chamber of the syringe barrel; a stopper slidably disposed within the chamber of the syringe barrel; and a plunger rod having a proximal end and a distal end engageable with a portion of the stopper; and a shell enclosing the syringe barrel, the shell comprising: a first shell portion having a proximal end, a distal end, and a first bottom wall; a second shell portion having a proximal end, a distal end, and a second bottom wall; and a hinge connected to a portion of the first bottom wall and a portion of the second bottom wall, the hinge connecting the first shell portion and the second shell portion together such that the shell is transitionable between an open position and a closed position in which the syringe barrel is enclosed within the first shell portion and the second shell portion.

In one configuration, a portion of the first shell portion is pivotable between a closed position and an open position. In another configuration, a portion of the first shell portion is pivotable between the closed position and the open position via a second hinge. In yet another configuration, with the shell in the closed position, the first shell portion and the second shell portion together define a syringe flange surrounding portion having a top wall that defines a first shell proximal aperture, a bottom wall, and a sidewall extending therebetween, and wherein the syringe flange surrounding portion encloses the flange of the syringe barrel therein. In one configuration, the syringe flange surrounding portion is disposed adjacent the proximal end of the first shell portion and the proximal end of the second shell portion. In another configuration, the plunger rod includes a plunger rod disk disposed between the proximal end of the plunger rod and the distal end of the plunger rod. In yet another configuration, a diameter of the plunger rod disk is greater than a diameter of the plunger rod. In one configuration, with the shell in the closed position, the first shell portion and the second shell portion together define a plunger rod disk surrounding portion having a top wall that defines a second shell proximal aperture, a bottom wall, and a sidewall extending therebetween, and wherein the plunger rod disk surrounding portion encloses the plunger rod disk therein. In another configuration, with the shell in the closed position, contact between the plunger rod disk and the plunger rod disk surrounding portion limits movement of the plunger rod in a distal direction and in a proximal direction. In yet another configuration, with the shell in the closed position, a portion of the plunger rod extends from the second shell proximal aperture. In one configuration, with the shell in the closed position, the first bottom wall overlaps the second bottom wall. In another configuration, with the shell in the closed position, the overlapping first and second bottom walls shield the distal end of the syringe barrel. In yet another configuration, one of the first shell portion and the second shell portion include a transparent window. In one configuration, with the shell in the open position, a longitudinal axis of the first shell portion and a longitudinal axis of the second shell portion are collinear.

In accordance with another embodiment of the present invention, a shell for enclosing a pre-filled syringe includes a first shell portion having a proximal end, a distal end, and a first bottom wall; a second shell portion having a proximal end, a distal end, and a second bottom wall; and a hinge connected to a portion of the first bottom wall and a portion of the second bottom wall, the hinge connecting the first shell portion and the second shell portion together such that the shell is transitionable between an open position and a closed position, wherein, with the shell in the closed position, the first shell portion and the second shell portion together define a syringe flange surrounding portion having a top wall that defines a first shell proximal aperture, a bottom wall, and a sidewall extending therebetween, wherein, with the shell in the closed position, the first shell portion and the second shell portion together define a plunger rod disk surrounding portion having a top wall that defines a second shell proximal aperture, a bottom wall, and a sidewall extending therebetween, and wherein, with the shell in the open position, a longitudinal axis of the first shell portion and a longitudinal axis of the second shell portion are collinear.

In one configuration, a portion of the first shell portion is pivotable between a closed position and an open position. In another configuration, a portion of the first shell portion is pivotable between the closed position and the open position via a second hinge. In yet another configuration, with the shell in the closed position, the first bottom wall overlaps the second bottom wall. In one configuration, one of the first shell portion and the second shell portion include a transparent window.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 21 is a front view of a plunger rod in accordance with another embodiment of the present invention.

FIG. 22 is a perspective view of a shell in accordance with an embodiment of the present invention.

FIG. 23 is a perspective view of a shell in accordance with an embodiment of the present invention.

FIG. 37 is a perspective view of a shell in accordance with another embodiment of the present invention.

FIG. 38 is a perspective view of a shell in accordance with another embodiment of the present invention.

FIG. 39 is a perspective view of a shell in accordance with another embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 2:
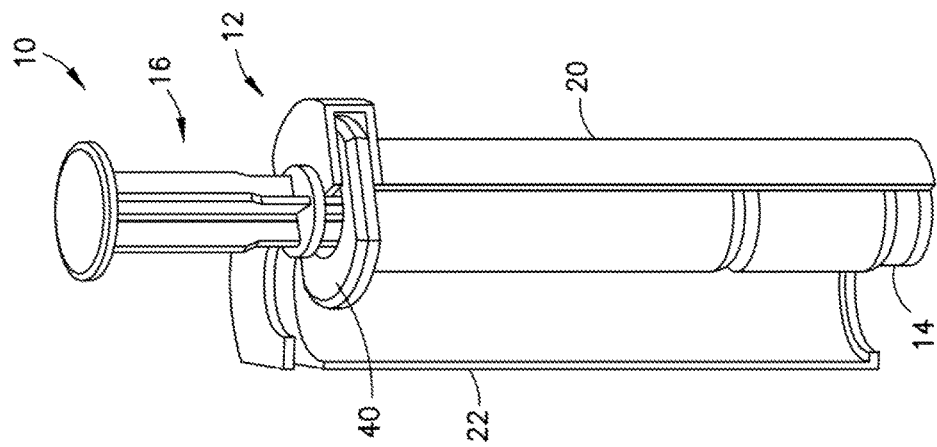
FIG. 2 is a partially assembled, perspective view of the syringe packaging system of FIG. 1 in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe or a syringe assembly adapted for contact with a patient and/or engagement with a separate device such as a needle assembly or IV connection assembly, and "proximal" refers to the opposite direction of distal, i.e., away from the end of a syringe or a syringe assembly adapted for engagement with the separate device. For purposes of this disclosure, the above-mentioned references are used in the description of the components of a syringe or a syringe assembly in accordance with the present disclosure.

Figure 25:
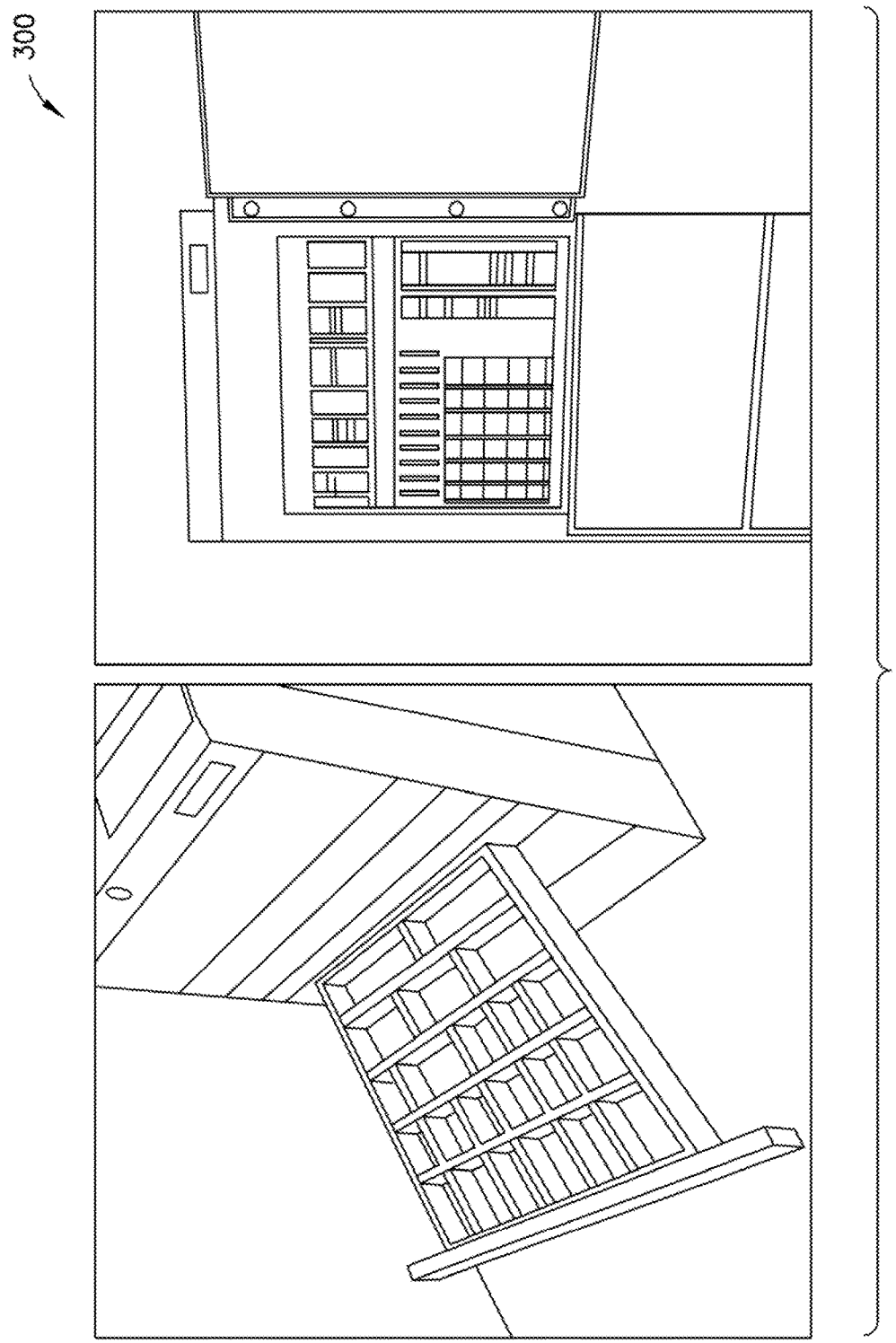
FIG. 25 is a perspective view of a plurality of automated dispensing cabinets.

FIGS. 1-17 illustrate an exemplary embodiment of the present disclosure. Referring to FIGS. 1-17, a syringe packaging system 10 includes a shell or sleeve 12; a syringe or a syringe assembly 13 including a syringe barrel 14, a plunger rod 16, and a stopper 19; and a label 18. The shell 12 of the syringe packaging system 10 provides a packaging member for a pre-filled syringe, such as syringe 13. The shell 12 of the present disclosure allows for reduced storage space of a pre-filled syringe. For example, the shell 12 allows for reduced storage space of a pre-filled syringe in an automated dispensing cabinet 300 (FIG. 25).

Figure 13:
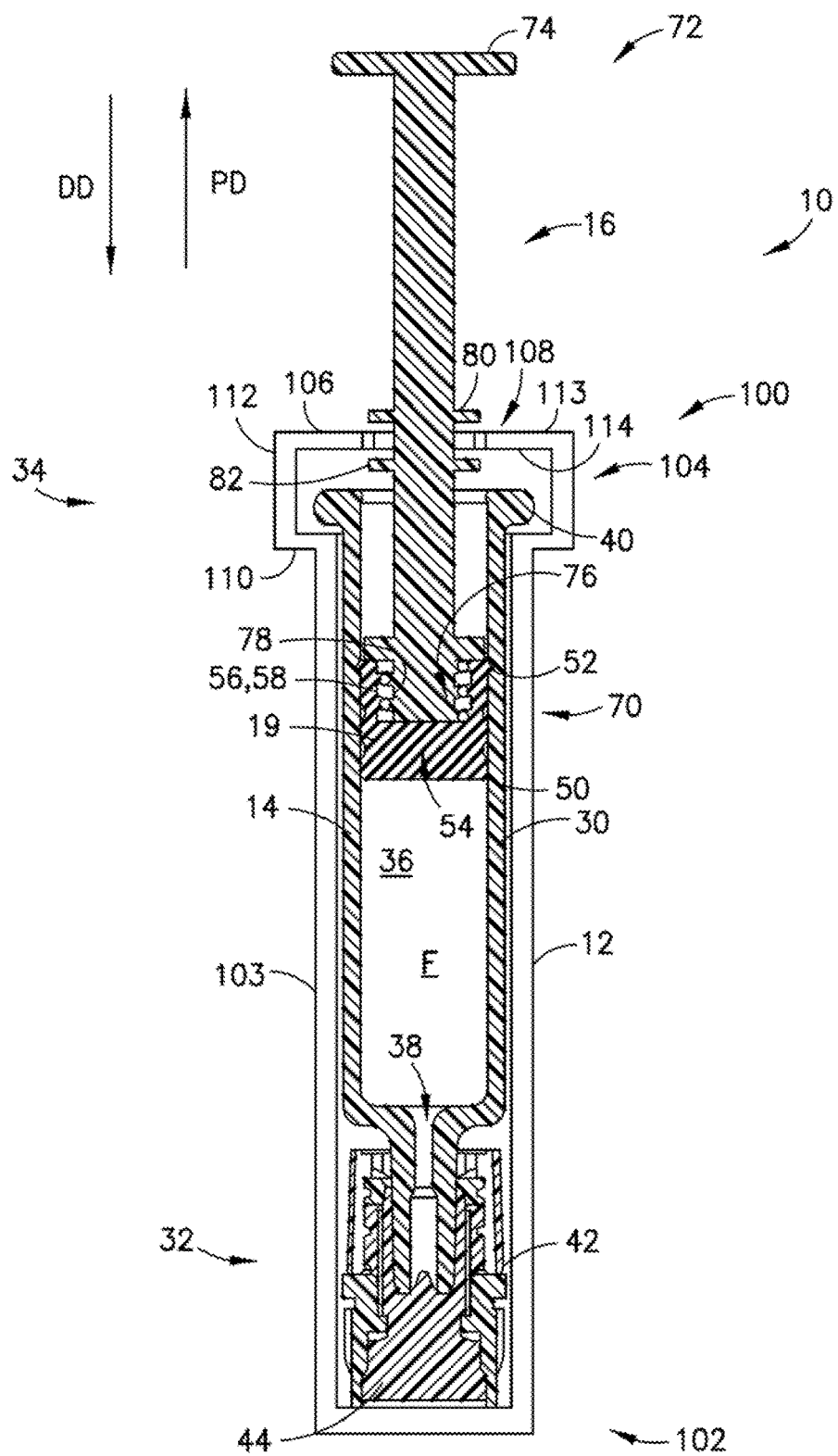
FIG. 13 is a cross-sectional view of a syringe packaging system in accordance with an embodiment of the present invention.
Figure 14:
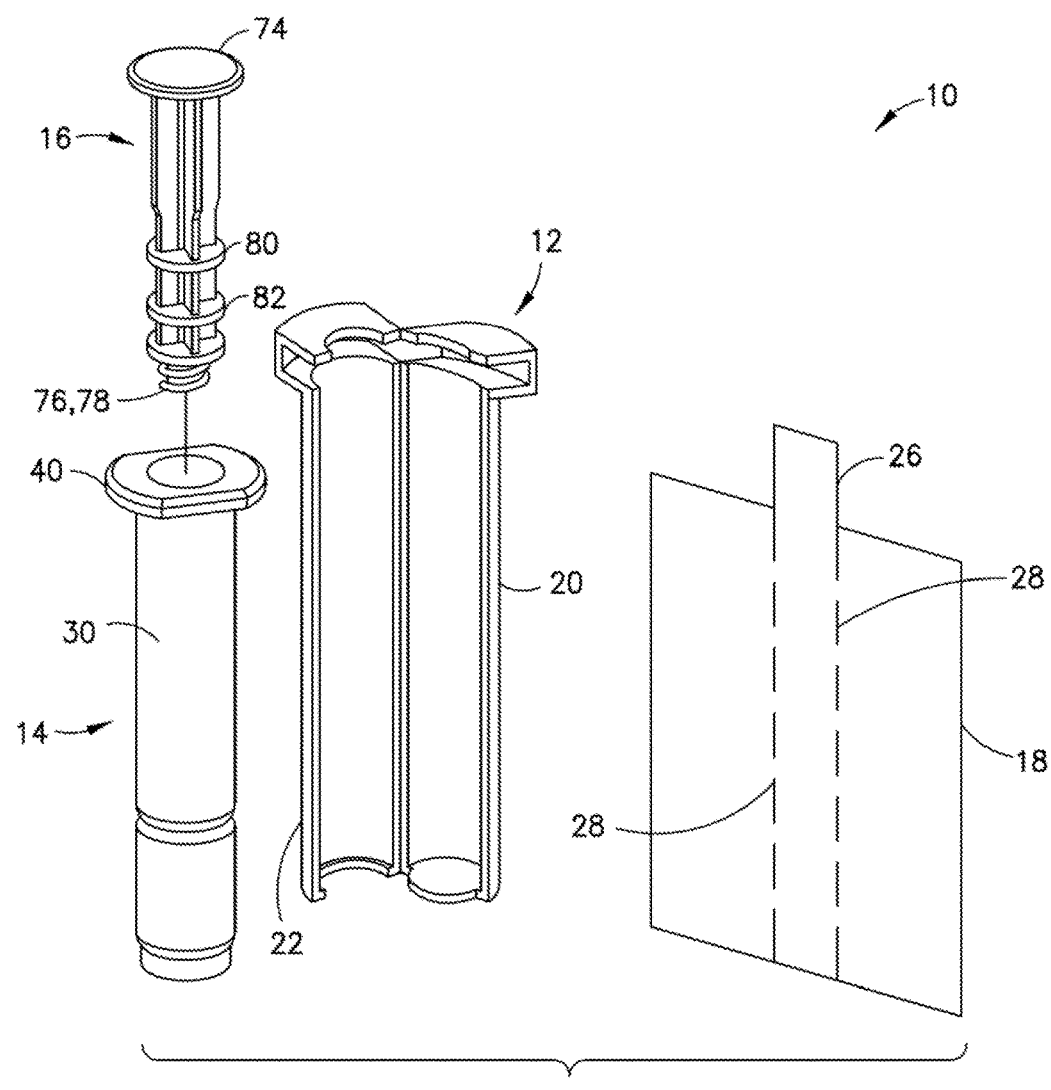
FIG. 14 is an exploded, perspective view of a syringe packaging system in accordance with an embodiment of the present invention.
Figure 15:
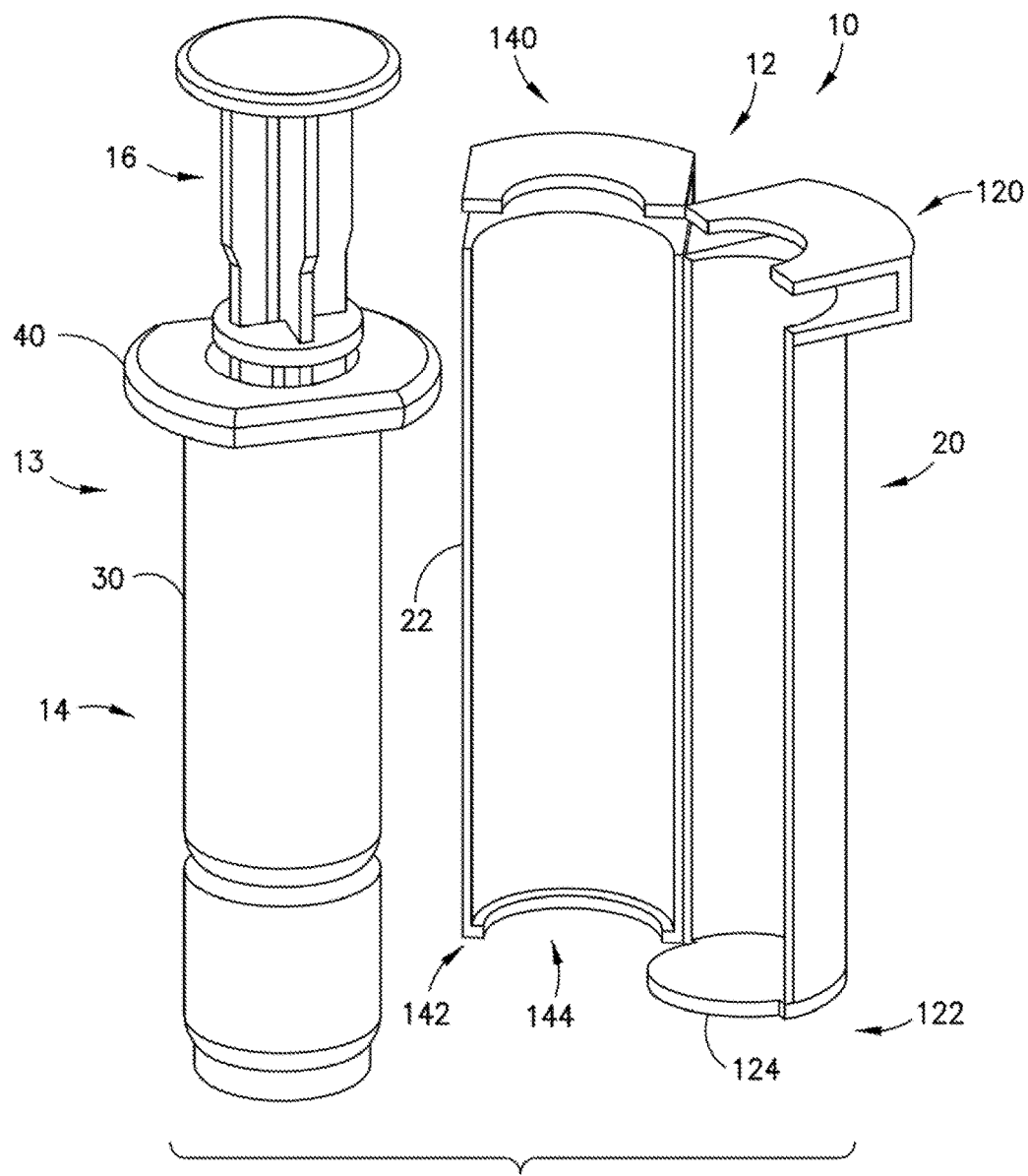
FIG. 15 is an exploded, perspective view of a syringe packaging system in accordance with an embodiment of the present invention.
Figure 16:
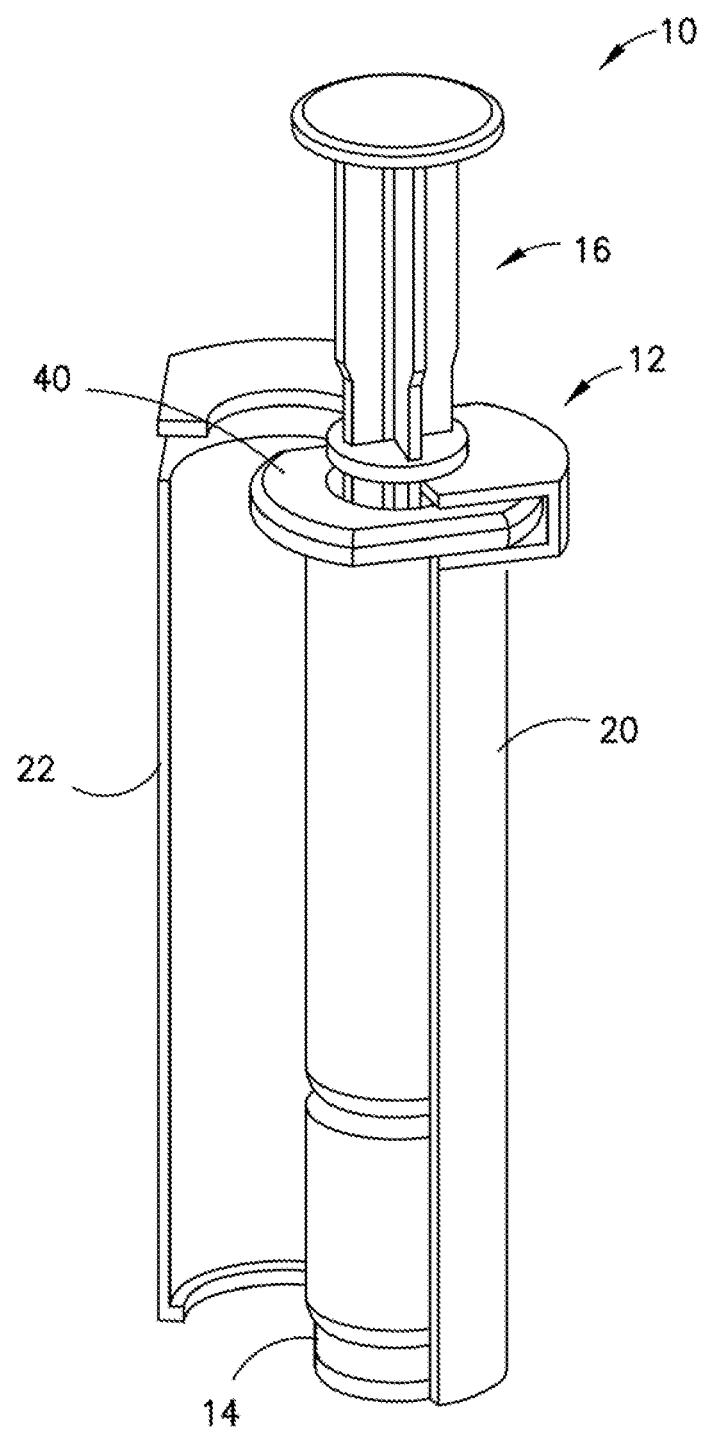
FIG. 16 is a partially assembled, perspective view of a syringe packaging system in accordance with an embodiment of the present invention.
Figure 17:
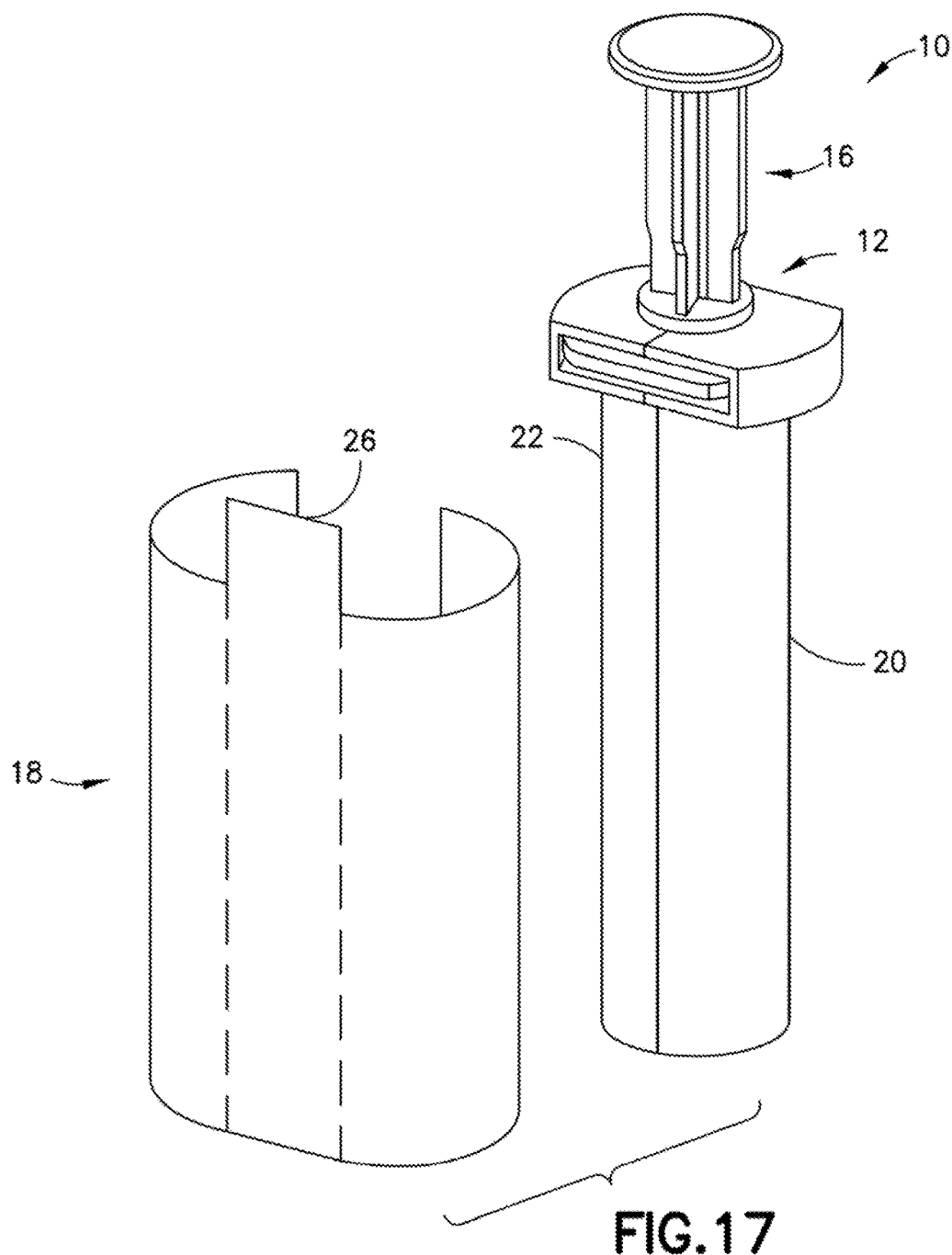
FIG. 17 is a partially assembled, perspective view of a syringe packaging system, with a label positioned to secure and connect a first shell portion and a second shell portion in accordance with an embodiment of the present invention.

Referring to FIG. 13, in one embodiment, syringe assembly 13 includes syringe barrel 14, plunger rod 16, and a stopper 19. Syringe assembly 13 may be adapted for dispensing and delivery of a fluid and/or collection of a fluid. For example, syringe assembly 13 may be used for injection or infusion of fluid such as a medication or drug into a patient. Syringe assembly 13 is contemplated for use in connection with a needle, such as by connecting syringe assembly 13 to a separate needle assembly (not shown), or alternatively for connection with an intravenous (IV) connection assembly (not shown). It can be appreciated that the present disclosure can be used with any type of syringe assembly, particularly those which are placed in a controlled storage environment in which storage space is limited. These types of syringes include traditional pre-filled syringe assemblies, metered dose syringes, aspiration syringes for withdrawing fluid from a patient or medication from a container, and the like.

In one embodiment, the shell 12 can be designed for a syringe 13 that is a cut flange syringe. In other embodiments, the shell 12 can be designed for a syringe 13 that is a round flange syringe. In other embodiments, the shell 12 can be designed for other syringes.

Referring to FIGS. 1-17, syringe barrel 14 generally includes a barrel body having a sidewall 30 extending between a first or distal end 32 and a second or proximal end 34. Sidewall 30 defines an elongate aperture or interior chamber 36 of syringe barrel 14. In one embodiment, interior chamber 36 may span the extent of syringe barrel 14 so that syringe barrel 14 is cannulated along its entire length. In one embodiment, syringe barrel 14 may be in the general form of an elongated cylindrical barrel as is known in the art in the general shape of a hypodermic syringe. In alternative embodiments, syringe barrel 14 may be in other forms for containing a fluid for delivery, such as in the general form of an elongated rectangular barrel, for example. Syringe barrel 14 may be formed of glass, or may be injection molded from thermoplastic material such as polypropylene and polyethylene according to techniques known to those of ordinary skill in the art, though it is to be appreciated that syringe barrel 14 may be made from other suitable materials and according to other applicable techniques. In certain configurations, syringe barrel 14 may include an outwardly extending flange 40 about at least a portion of proximal end 34. Flange 40 may be configured for easy grasping by a medical practitioner, as will be discussed herein.

Distal end 32 of syringe barrel 14 includes an outlet opening 38 (FIG. 13) which is in fluid communication with chamber 36. Outlet opening 38 may be sized and adapted for engagement with a separate device, such as a needle assembly or IV connection assembly and, therefore, may include a mechanism for such engagement as is conventionally known. For example, distal end 32 may include a generally-tapered luer tip for engagement with an optional separate tapered luer structure of such a separate device for attachment therewith (not shown). In one configuration, both the tapered luer tip and the separate tapered luer structure may be provided with the syringe assembly 13. In such a configuration, the separate tapered luer structure may be fitted with an attachment mechanism, such as a threaded engagement, for corresponding engagement with a separate device (not shown). In another configuration, the tapered luer tip may be provided for direct engagement with a separate device (not shown). In addition, a mechanism for locking engagement therebetween may also be provided with at least one of the tapered luer tip and/or the separate tapered luer structure, such as a luer collar or luer lock including interior threads. Such luer connections and luer locking mechanisms are well known in the art.

Proximal end 34 of syringe barrel 14 is generally open-ended, but is intended to be closed off to the external environment as discussed herein. Syringe barrel 14 may also include markings, such as graduations located on sidewall 30, for providing an indication as to the level or amount of fluid contained within interior chamber 36 of syringe barrel 14. Such markings may be provided on an external surface of sidewall 30, an internal surface of sidewall 30, or integrally formed or otherwise within sidewall 30 of syringe barrel 14. In other embodiments, alternatively, or in addition thereto, the markings may also provide a description of the contents of the syringe or other identifying information as may be known in the art, such as maximum and/or minimum fill lines.

Syringe barrel 14 may be useful as a pre-filled syringe, and, therefore, may be provided for end use with a fluid F (FIG. 13), such as a medication or drug, contained within interior chamber 36 of syringe barrel 14, pre-filled by the manufacturer. In this manner, syringe barrel 14 can be manufactured, pre-filled with a medication, sterilized, and packaged in appropriate packaging such as shell 12 for delivery, storage, and use by the end user, without the need for the end user to fill the syringe with medication from a separate vial prior to use. In one embodiment, syringe barrel 14 may include a tip cap or sealing cap member 42 including a seal 44 disposed at distal end 32 of syringe barrel 14 to seal a fluid F, such as a medication, within interior chamber 36 of syringe barrel 14. In one embodiment, seal 44 may be formed of a pierceable elastomer material.

As used herein, the term "drug" and/or "medication" refers to a pharmaceutically active ingredient(s) and any pharmaceutical liquid composition containing the pharmaceutically active ingredient(s). Pharmaceutical liquid compositions include forms such as solutions, suspensions, emulsions, and the like. These pharmaceutical liquid compositions can be administered orally or by injection.

Referring to FIG. 13, syringe assembly 13 includes stopper 19 which is moveably or slidably disposed within interior chamber 36 of syringe barrel 14, and in sealing contact with the internal surface of sidewall 30 of syringe barrel 14. Stopper 19 is sized relative to syringe barrel 14 to provide sealing engagement with the interior surface of sidewall 30 of syringe barrel 14. Additionally, stopper 19 may include one or more annular ribs extending around the periphery of stopper 19 to increase the sealing engagement between stopper 19 and the interior surface of sidewall 30 of syringe barrel 14. In alternate embodiments, a singular O-ring or a plurality of O-rings may be circumferentially disposed about stopper 19 to increase the sealing engagement with the interior surface of sidewall 30 of syringe barrel 14.

Referring to FIG. 13, in one embodiment, stopper 19 includes a first or distal end 50 and a second or proximal end 52 defining a plunger receiving aperture 54 formed therein and having a securement feature or engagement portion 56 for securing plunger rod 16 to stopper 19. In one embodiment, referring to FIG. 13, the engagement portion 56 may include a threaded portion 58.

Referring to FIG. 13, syringe assembly 13 further includes plunger rod 16 which provides a mechanism for dispensing fluid contained within interior chamber 36 of syringe barrel 14 through outlet opening 38 upon connection of plunger rod 16 to syringe barrel 14 via stopper 19 as will be described in more detail below. Plunger rod 16 is adapted for advancing stopper 19. In one embodiment, plunger rod 16 is sized for movement within interior chamber 36 of syringe barrel 14 as will be discussed in more detail below, and generally includes a first or distal end 70, a second or proximal end 72, a flange 74 disposed adjacent second end 72, a securement feature or engagement portion 76 for securing plunger rod 16 to stopper 19, a proximal disk 80, and a distal disk 82. In one embodiment, referring to FIG. 13, the engagement portion 76 of plunger rod 16 may include a threaded portion 78. In one embodiment, the flange 74 forms a thumb pad for a user to manipulate the plunger rod 16. In one embodiment, the engagement portion 76 is disposed adjacent the first end 70.

In one embodiment, plunger rod 16 can be secured to stopper 19 by threadingly engaging threaded portion 58 of stopper 19 to threaded portion 78 of plunger rod 16 as shown in FIG. 13. In other embodiments, plunger rod 16 can be secured to stopper 19 using a snap fit mechanism, a ball detent, locking tabs, spring loaded locking mechanism, latch, adhesive, or other similar mechanism. In all embodiments, plunger rod 16 is locked, secured, or engaged to stopper 19, i.e., significant relative movement between plunger rod 16 and stopper 19 is limited and/or prevented.

In some embodiments, plunger rod 16 and stopper 19 may be co-formed such as by co-extrusion. In other embodiments, plunger rod 16 and stopper 19 may be integrally formed as a plunger/stopper assembly.

Figure 18:
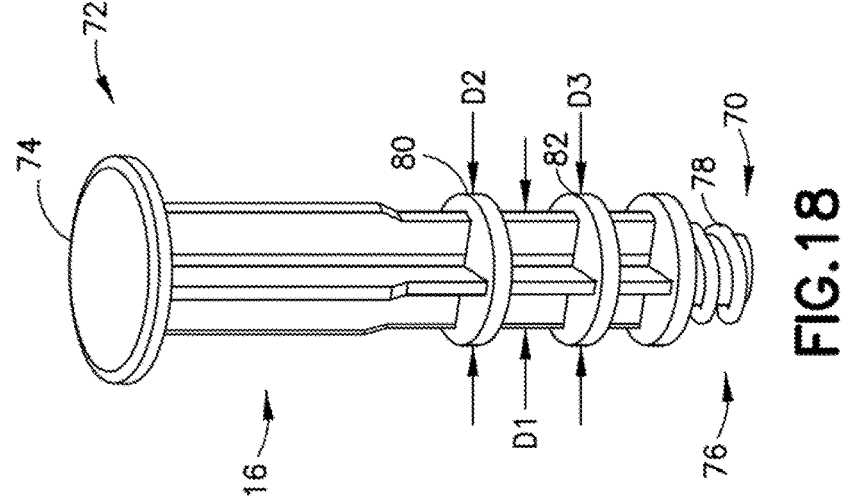
FIG. 18 is a perspective view of a plunger rod in accordance with an embodiment of the present invention.
Figure 24:
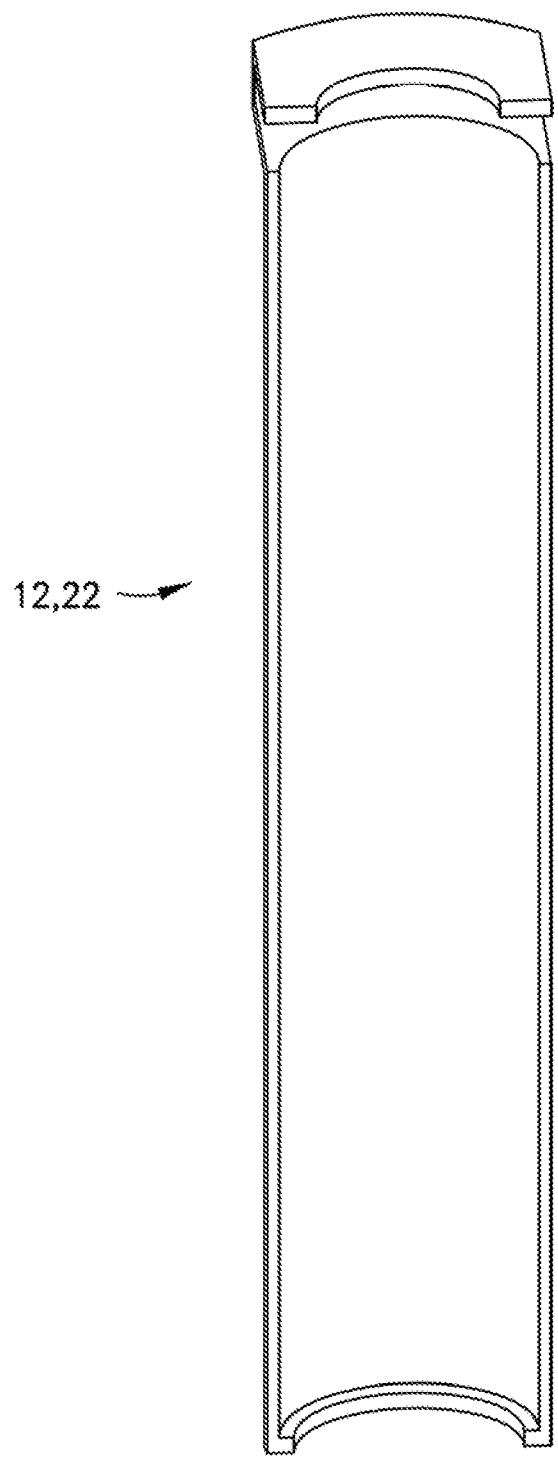
FIG. 24 is an elevation view of a portion of a shell in accordance with an embodiment of the present invention.

Referring to FIGS. 13 and 18, the plunger rod 16 includes a proximal disk 80 and a distal disk 82. Referring to FIG. 18, the plunger rod 16 has a plunger rod diameter D1, the proximal disk 80 has a proximal disk diameter D2, and the distal disk 82 has a distal disk diameter D3. In one embodiment, the proximal disk diameter D2 is greater than the plunger rod diameter D1. In one embodiment, the distal disk diameter D3 is greater than the plunger rod diameter D1. In this manner, with the syringe barrel 14 enclosed within the shell 12, the proximal disk 80 of the plunger rod 16 limits and/or prevents movement of the plunger rod 16 in a distal direction DD (FIG. 13) and the distal disk 82 of the plunger rod 16 limits and/or prevents movement of the plunger rod 16 in a proximal direction PD (FIG. 13) as described in more detail below. Referring to FIGS. 13 and 18, the distal disk 82 is spaced from the proximal disk 80. In one embodiment, the proximal disk 80 is disposed between the distal disk 82 and the proximal end 72, and the distal disk 82 is disposed between the proximal disk 80 and the distal end 70.

Figure 20:
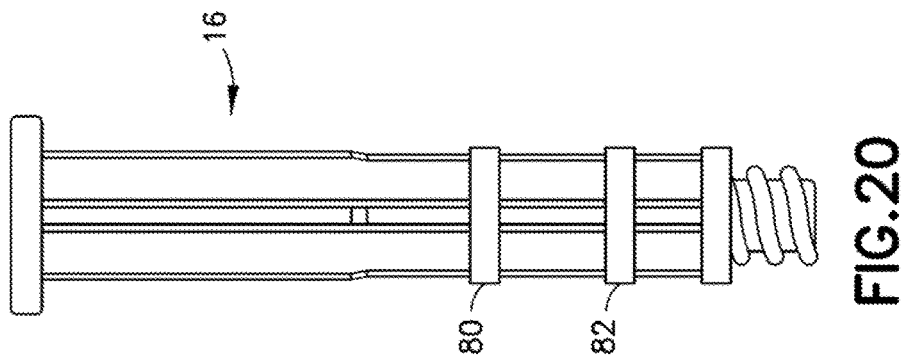
FIG. 20 is a front view of a plunger rod in accordance with an embodiment of the present invention.
Figure 19:
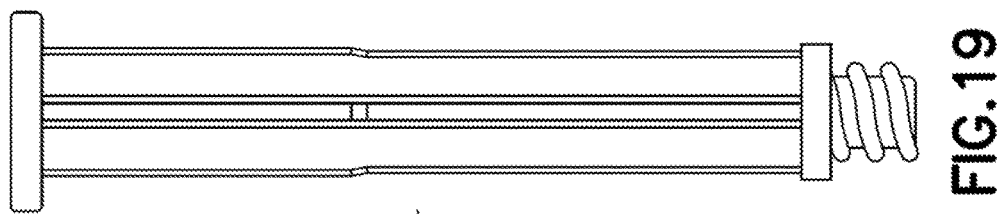
FIG. 19 is a front view of a standard plunger rod.

Referring to FIGS. 19 and 20, in one embodiment, the length of a plunger rod 16 of the present disclosure (FIG. 20) is shorter than the length of a conventional or standard plunger rod 200 (FIG. 19). In this manner, a plunger rod 16 of the present disclosure allows for reduced storage space of a pre-filled syringe.

Additionally, at the end of the injection, when the entire drug has been delivered, the thumb pad or flange 74 of the plunger rod 16 of the present disclosure is much closer to the flange 40 of the syringe barrel 14 than a standard syringe is. For example, in one embodiment, the distance between an upper surface of the flange 40 of the syringe barrel 14 and a lower surface of the flange 74 of the plunger rod 16 may be between 0.5 to 2.5 mm. In another embodiment, the distance between an upper surface of the flange 40 of the syringe barrel 14 and a lower surface of the flange 74 of the plunger rod 16 may be between 0.9 to 2.3 mm. In another embodiment, the distance between an upper surface of the flange 40 of the syringe barrel 14 and a lower surface of the flange 74 of the plunger rod 16 may be around 1.6 mm. In this manner, the global length of a prefilled syringe is reduced, leading to a smaller required space for storage.

In another embodiment, the plunger rod 16 does not contain any disks and includes a notch 86 (FIG. 21) that is positioned on a length of the plunger rod 16. The position and the width of the notch 86 is calculated with a stack-up analysis considering the tolerance of each dimension of the syringe.

Referring to FIG. 21, in another embodiment, the plunger rod 16 includes one disk 88 and a notch 86.

With any plunger rod 16 of the present disclosure, it is possible to rotate the syringe 13 inside the sleeve 12 to read the information written on the syringe barrel 14 through a transparent portion of the sleeve 12, i.e., the viewing window 116 (FIG. 11), or to see the integrity of a liquid contained inside the syringe 13, thanks to the area of the sleeve 12 that is not covered by any label 18.

Referring to FIGS. 1-13, a shell 12 of the present disclosure encloses the syringe barrel 14 and includes a proximal end 100, a distal end 102, and a sidewall 103 extending therebetween. In one embodiment, the proximal end 100 includes a syringe flange surrounding portion 104 that includes a top wall 106 that defines a shell proximal aperture 108, a bottom wall 110, and a sidewall 112 extending therebetween. The shell 12 of the present invention provides a mechanical protection of the syringe 13 that is contained inside. The shell 12 also provides a good support for labeling as described in more detail below. In one embodiment, the thickness of the sidewall 103 of the shell 12 may be between 0.5 mm and 1 mm.

Referring to FIGS. 1-17 and 22-24, in one embodiment, a shell 12 of the present disclosure includes a first shell portion 20 and a second shell portion 22 for enclosing the syringe barrel 14 as shown in FIG. 13. The first shell portion 20 includes a proximal end 120 and a distal end 122 having a disk-shaped bottom portion 124. The second shell portion 22 includes a proximal end 140 and a distal end 142 defining an open bottom 144.

Referring to FIG. 13, with the first shell portion 20 engaged with the second shell portion 22 to form the shell 12, the proximal end 120 of the first shell portion 20 and the proximal end 140 of the second shell portion 22 together define a syringe flange surrounding portion 104 that includes a top wall 106 that defines a shell proximal aperture 108, a bottom wall 110, and a sidewall 112 extending therebetween. The syringe flange surrounding portion 104 encloses the flange 40 of the syringe barrel 14 as shown in FIG. 13.

In one embodiment, shell 12, e.g., first shell portion 20 and second shell portion 22, is formed of a plastic material. For example, shell 12, e.g., first shell portion 20 and second shell portion 22, may be formed of polyethylene terephthalate (PET), polypropylene (PP), polycarbonate (PC), or other material. In one embodiment, shell 12, e.g., first shell portion 20 and second shell portion 22, is formed of a transparent material. In this manner, referring to FIG. 11, a portion of the shell 12 forms a viewing window 116 that allows a user to see data and/or information written on an outer surface of the syringe barrel 14.

The first shell portion 20 and the second shell portion 22 are each designed so that when they are assembled together they form a global tube or shell 12 to receive a pre-filled syringe 13. In one embodiment, with the first shell portion 20 engaged with the second shell portion 22 to form the shell 12, the disk-shaped bottom portion 124 of the first shell portion 20 closes the open bottom 144 of the second shell portion 22.

In this particular configuration, the distal end 122 of the first shell portion 20 has a bottom in the form of a disk, i.e., the disk-shaped bottom portion 124, that matches the open bottom 144 of the distal end 142 of the second shell portion 22. In such an embodiment, the disk-shaped bottom portion 124 acts as a barrier to avoid any piercing and/or withdrawal of a drug contained inside the syringe 13 through a seal 44 of the pre-filled syringe 13, with a needle, for example. In this manner, with the syringe barrel 14 enclosed within the shell 12, the disk-shaped bottom portion 124 of the first shell portion 20 shields the distal end 32 and the seal 44 of the syringe barrel 14. The shell 12 prevents any piercing of the syringe barrel 14 and avoids any withdrawal of a drug contained inside the syringe barrel 14.

In another embodiment, the distal end 122 of the first shell portion 20 and the distal end 142 of the second shell portion 22 could have identical half-disk shaped bottom portions.

In another embodiment, the distal end 122 of the first shell portion 20 has a half-disk bottom portion with a thickness t and the distal end 142 of the second shell portion 22 has a full-disk with a step in thickness. For example, the thinner portion could have a thickness t' while the thicker portion could have a thickness that corresponds to the global thickness t+t'. In this configuration, no needle access to a drug contained inside the syringe 13 through a seal 44 of the pre-filled syringe 13 is allowed. In one embodiment, the thickness of the bottom portion of the shell 12 is at least 1 mm. In another embodiment, the thickness of the bottom portion of the shell 12 is between 1 mm and 1.2 mm.

Referring to FIG. 13, the interaction between the syringe flange surrounding portion 104 and the flange 40 of the syringe barrel 14 will now be described.

In one embodiment, as described above, the proximal end 100 of shell 12 includes a syringe flange surrounding portion 104 that includes a top wall 106 that defines a shell proximal aperture 108, a bottom wall 110, and a sidewall 112 extending therebetween. The top wall 106 defines an upper surface 113 and a lower surface 114.

Referring to FIG. 13, with the syringe barrel 14 enclosed within the shell 12, the syringe flange surrounding portion 104 encloses the flange 40 of the syringe barrel 14 therein.

In such an embodiment, the flange 40 of the syringe barrel 14 is contained inside the surrounding syringe flange surrounding portion 104 of the shell 12 leading to mechanical retention of the plunger rod 16 as described in more detail below. The thickness of the syringe flange surrounding portion 104 is an important design parameter as no deformation of the surrounding syringe flange surrounding portion 104 is allowed to avoid plunger rod 16 withdrawal. In one embodiment, the thickness of the walls of the syringe flange surrounding portion 104 are at least 1 mm.

Referring to FIG. 13, the interaction between the proximal end 100 of the shell 12 and the plunger rod 16 will now be described. With the syringe barrel 14 enclosed within the shell 12, a portion of the plunger rod 16 extends from the shell proximal aperture 108. The shell proximal aperture 108 only allows passage of a portion of the plunger rod 16. The syringe flange surrounding portion 104 acts as a barrier to avoid any piercing and/or withdrawal of a drug contained inside the syringe 13 through a stopper 19 of the pre-filled syringe 13, with a needle, for example. In this manner, with the syringe barrel 14 enclosed within the shell 12, the syringe flange surrounding portion 104 of the shell 12 shields the syringe barrel 14. The shell 12 prevents any piercing of the syringe barrel 14 and stopper 19 and avoids any withdrawal of a drug contained inside the syringe barrel 14.

Referring to FIG. 13, with the syringe barrel 14 enclosed within the shell 12, the proximal disk 80 of the plunger rod 16 is positioned outside of the shell 12 and the distal disk 82 of the plunger rod 16 is positioned within the syringe flange surrounding portion 104. In this configuration, with the syringe barrel 14 enclosed within the shell 12, the proximal disk 80 of the plunger rod 16 prevents movement of the plunger rod 16 in a distal direction DD. Also, in this configuration, with the syringe barrel 14 enclosed within the shell 12, the distal disk 82 of the plunger rod 16 prevents movement of the plunger rod 16 in a proximal direction PD. For example, contact between the proximal disk 80 and the upper surface 113 of the top wall 106 prevents movement of the plunger rod 16 in the distal direction DD and contact between the distal disk 82 and the lower surface 114 of the top wall 106 prevents movement of the plunger rod 16 in the proximal direction PD.

The proximal disk 80 of the plunger rod 16 preventing movement of the plunger rod 16 in a distal direction DD prevents any leakage that should occur when high pressures are applied on the plunger rod 16 leading to sterility breakage.

The distal disk 82 of the plunger rod 16 preventing movement of the plunger rod 16 in a proximal direction PD provides three different functions. First, the distal disk 82 of the plunger rod 16 avoids the withdrawal of the plunger rod 16, e.g., the distal disk 82 of the plunger rod 16 avoids any movements of the plunger rod 16 in the proximal direction PD. Second, the distal disk 82 of the plunger rod 16 provides tamper evidence feature as the distal disk 82 of the plunger rod 16 ensures that the plunger rod 16 cannot be replaced if it has been removed. Also, the distal disk 82 of the plunger rod 16 guarantees the sterility of the product as it limits the displacement of the stopper 19 during transportation, e.g., the remaining bubble always present inside the container can be put under pressure during air transportation and lead to sterility loss.

In one embodiment, the position of the proximal disk 80 and the distal disk 82 can be calculated with a stack-up analysis considering the tolerance of each dimension of the syringe.

Figure 11:
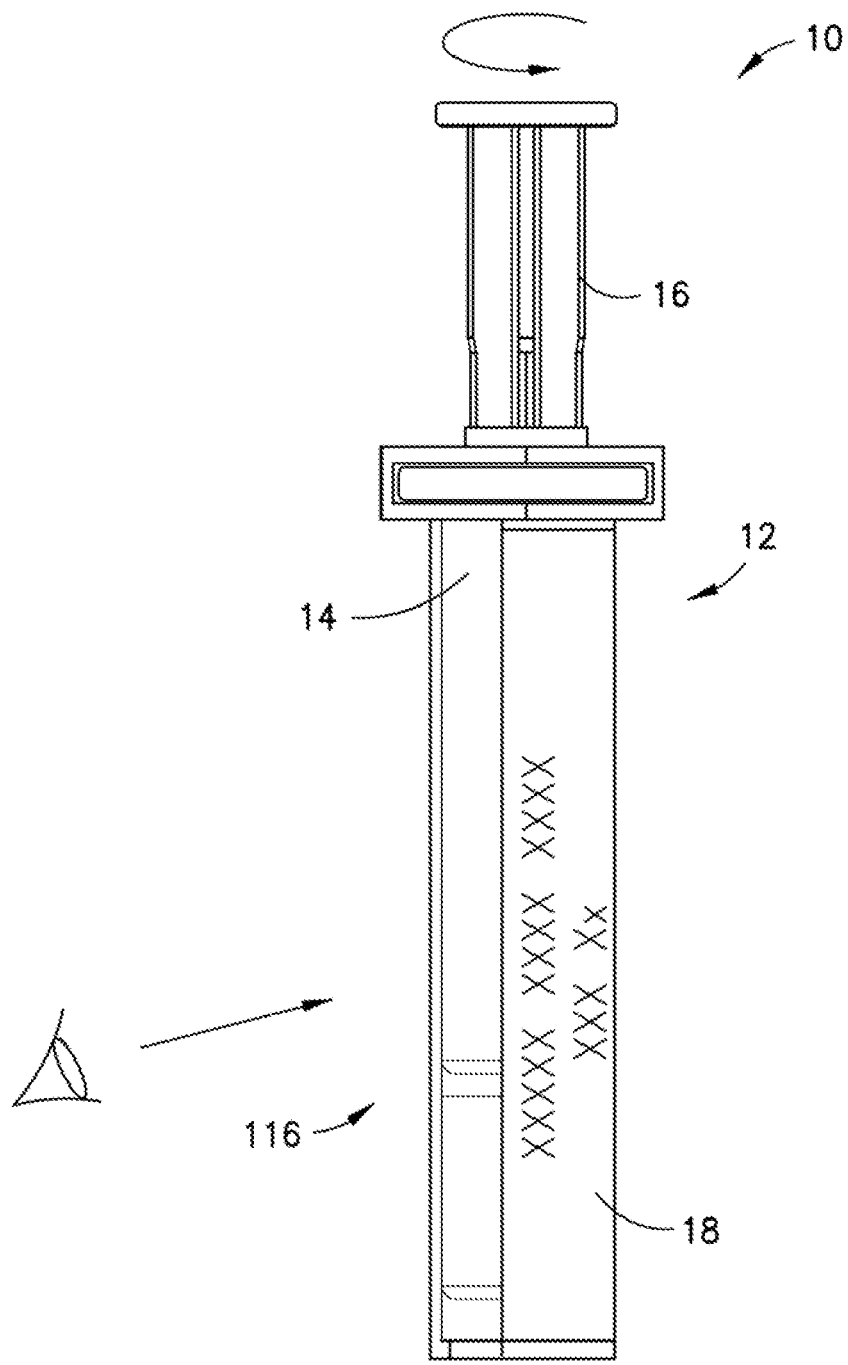
FIG. 11 is an elevation view of a viewing window of a syringe packaging system in accordance with an embodiment of the present invention.
Figure 12:
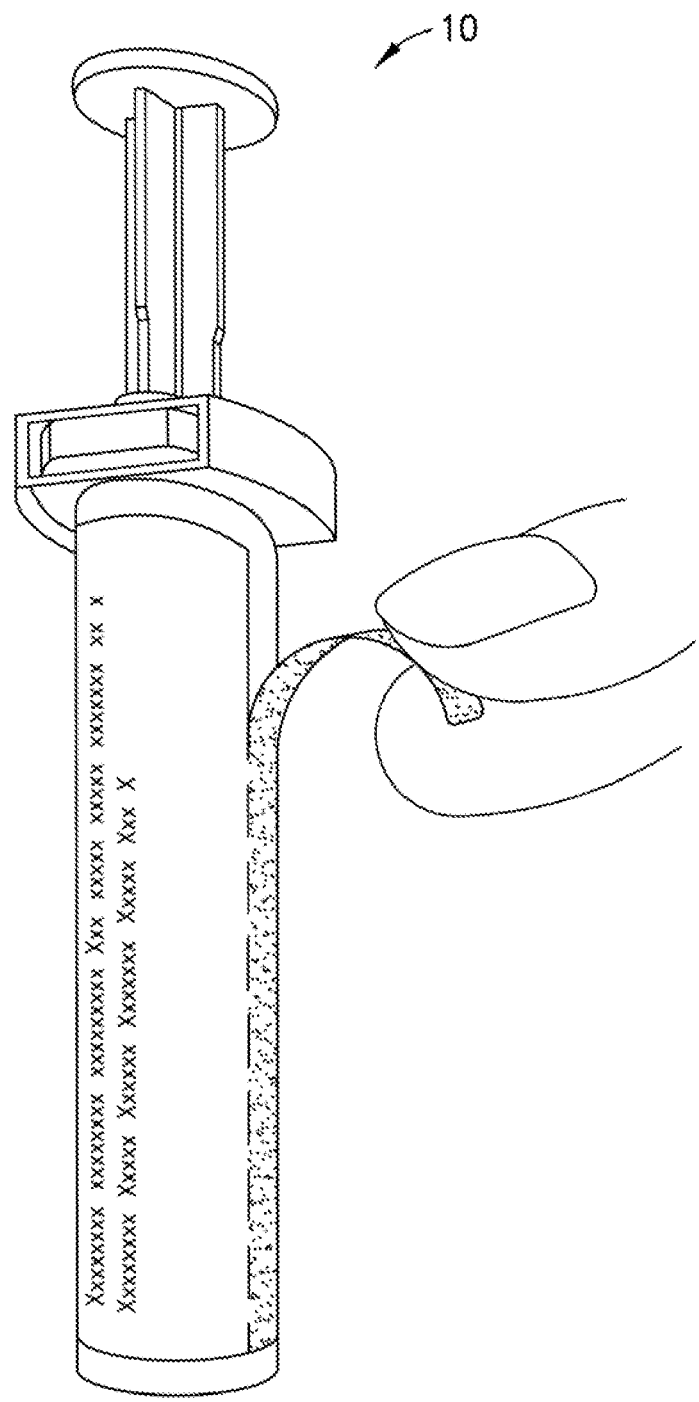
FIG. 12 is a perspective view of a syringe packaging system in accordance with an embodiment of the present invention.

Additionally, referring to FIGS. 11 and 13, with the syringe 13 enclosed within the shell 12, the shell proximal aperture 108 has a specific diameter to allow for the free rotation of the plunger rod 16 and the syringe 13. In this manner, for example, when a nurse wants to control the integrity of the product and read information present on a label affixed to a surface of the syringe barrel 14, she will be able to rotate the syringe 13 by rotating the plunger rod 16. Additionally, the syringe flange surrounding portion 104 is sized to minimize storage space but provide flange protection to the flange 40 of the syringe barrel 14 and to prevent any flange breakage.

Referring to FIGS. 13 and 18, the proximal disk diameter D2 and the distal disk diameter D3 are sized to contact the top wall 106 of the shell 12, with the syringe barrel 14 enclosed within the shell 12, to prevent movement of the plunger rod 16 in a distal direction DD and a proximal direction PD, as described above. However, the proximal disk diameter D2 and the distal disk diameter D3 are sized such that with the syringe barrel 14 removed from the shell 12, the plunger rod 16 is adapted to advance stopper 19 and plunger rod 16 is sized for movement within interior chamber 36 of syringe barrel 14, i.e., the proximal disk diameter D2 and the distal disk diameter D3 can slide within the syringe barrel 14.

Referring to FIGS. 1-17, the syringe packaging system 10 includes a sticker or a label 18. The label 18 is securable to a portion of the first shell portion 20 and to a portion of the second shell portion 22 to connect the first shell portion 20 and the second shell portion 22 with the syringe barrel 14 enclosed within the first shell portion 20 and the second shell portion 22.

The label 18 acts not only as a support for required regulatory information but as well as a hinge between the two plastic parts, e.g., the first and second shell portions 20, 22, thereby forming a single piece, e.g., the shell 12, that is able to protect the syringe 13.

Additionally, the label 18 includes a pre-perforated pull tab strip 26 that provides tamper evidence and is proof of the package integrity maintenance as the pull tab strip 26 needs to be pulled and removed for opening the shell 12 and giving access to the pre-filled syringe 13. In one embodiment, the label 18 has an easy opening with two vertical pre-cut perforations 28 with a chevron style cutting along the length of the label 18, which are also tamper evidence means.

All of the components of syringe packaging system 10 may be constructed of any known material, and are desirably constructed of medical-grade polymers.

Referring to FIGS. 1-6, packaging of a syringe 13 within shell 12 will now be described. Initially, syringe barrel 14, plunger rod 16, and shell 12 are sterilized according to techniques known to those of ordinary skill in the art. In some embodiments, syringe barrel 14 may be pre-filled as described above.

Figure 1:
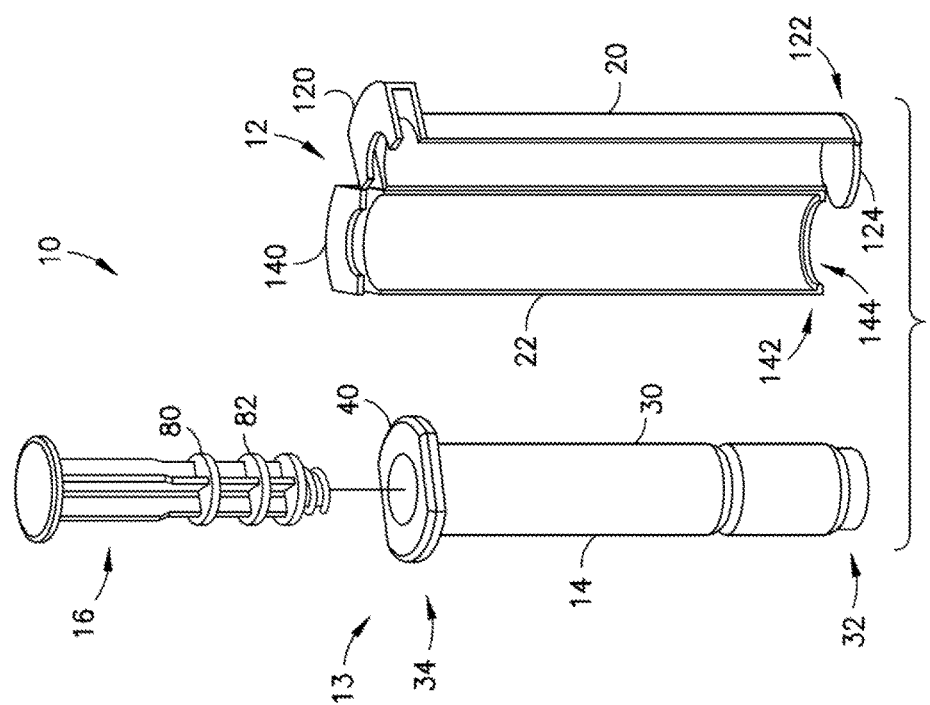
FIG. 1 is an exploded, perspective view of a syringe packaging system in accordance with an embodiment of the present invention.
Figure 3:
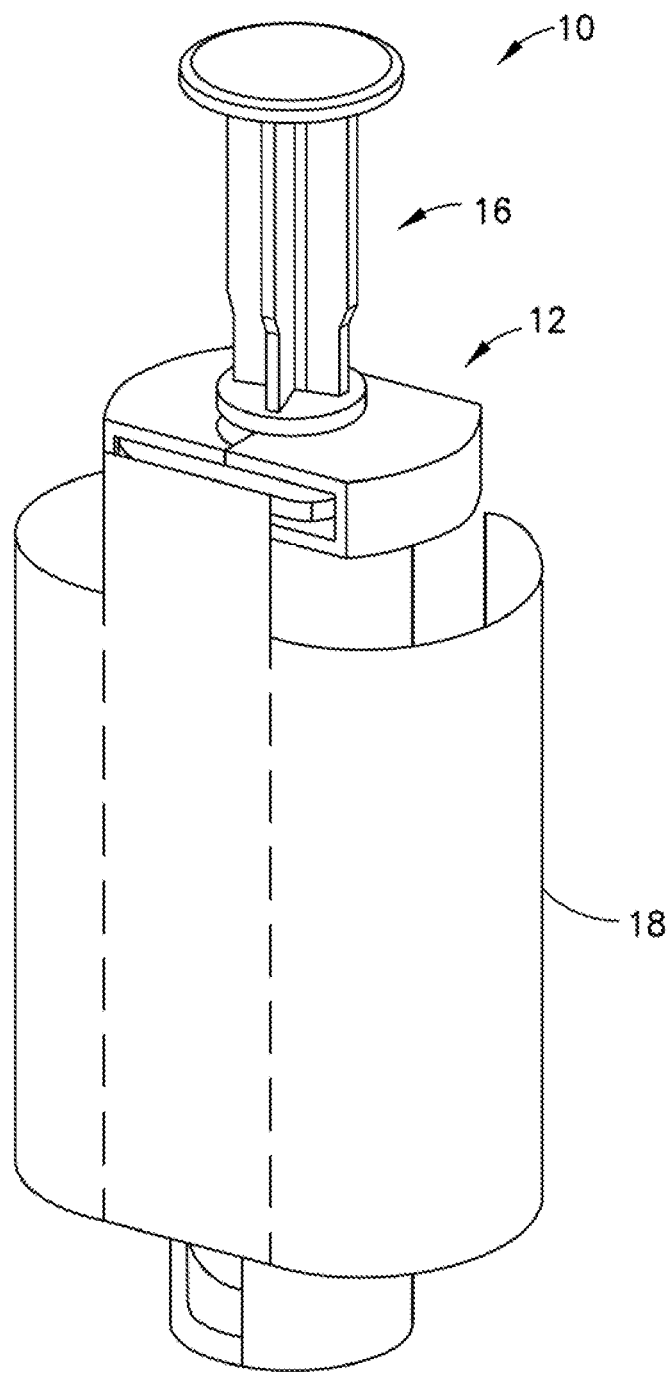
FIG. 3 is a partially assembled, perspective view of the syringe packaging system of FIG. 1, with a label positioned to secure and connect a first shell portion and a second shell portion in accordance with an embodiment of the present invention.
Figure 4:
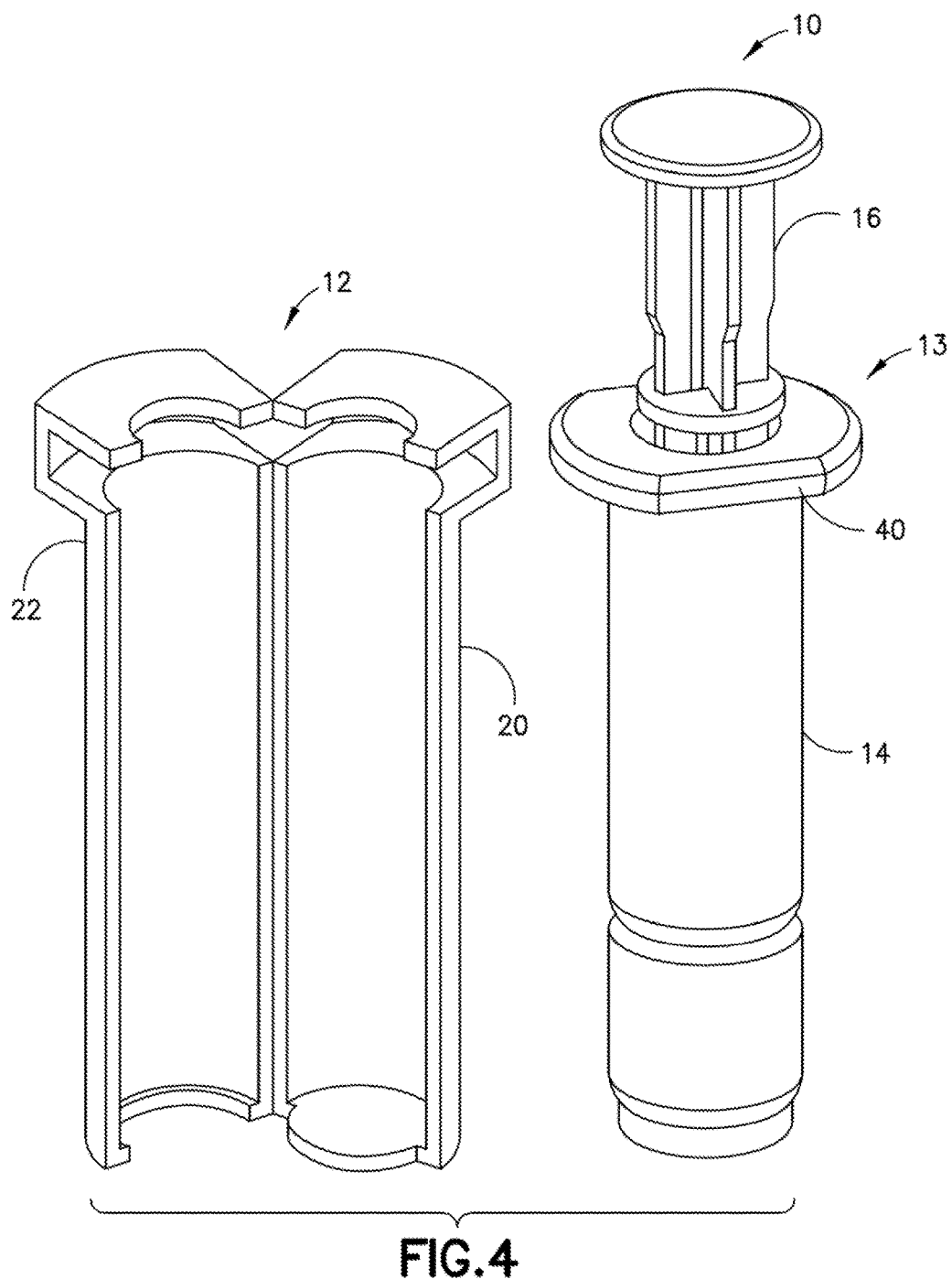
FIG. 4 is an exploded, perspective view of a syringe packaging system in accordance with an embodiment of the present invention.
Figure 5:
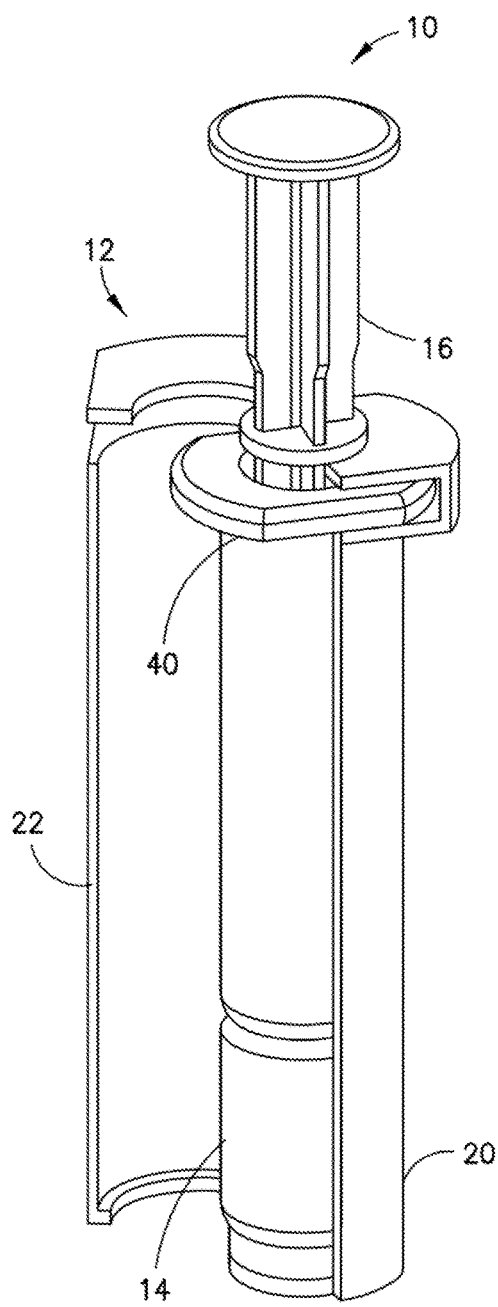
FIG. 5 is a partially assembled, perspective view of the syringe packaging system of FIG. 4 in accordance with an embodiment of the present invention.
Figure 6:
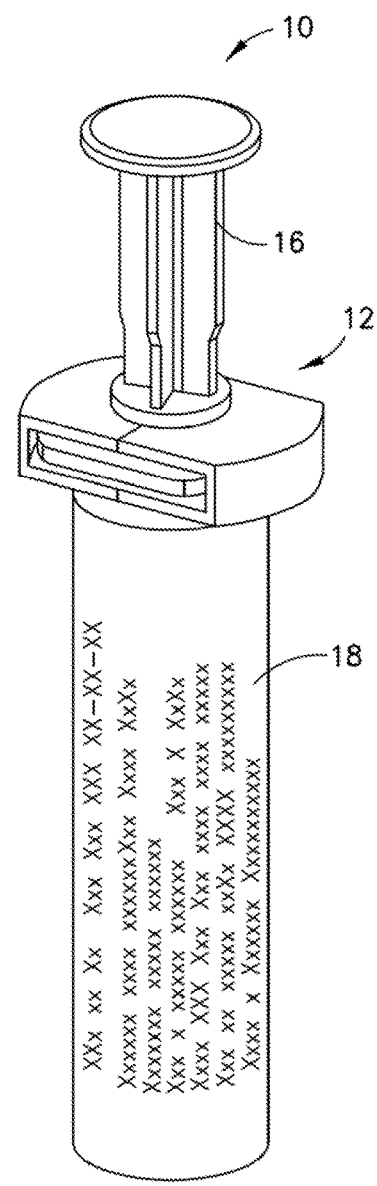
FIG. 6 is a partially assembled, perspective view of the syringe packaging system of FIG. 4, with a label connecting a first shell portion and a second shell portion in accordance with an embodiment of the present invention.
Figure 7:
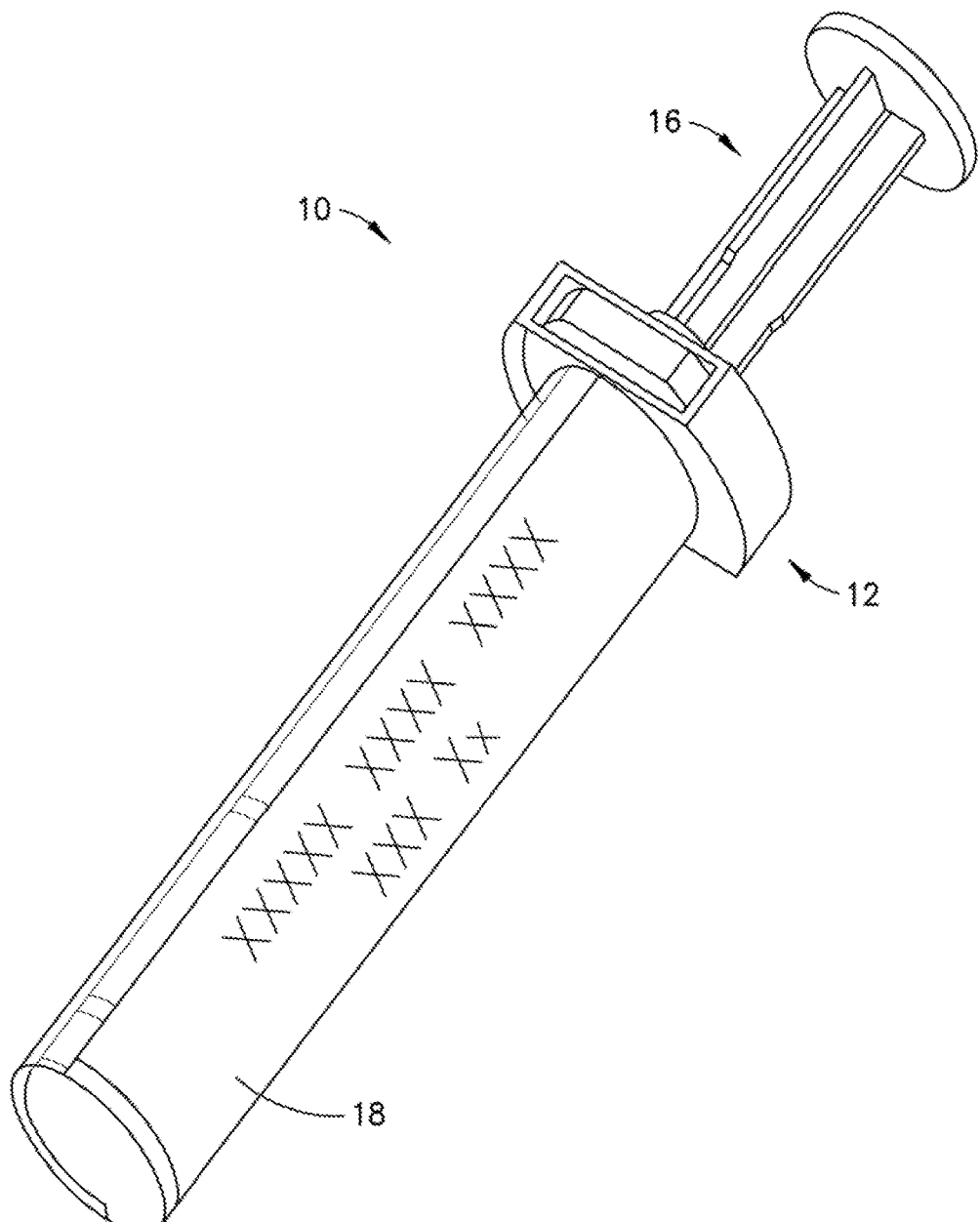
FIG. 7 is a perspective view of a syringe packaging system in accordance with an embodiment of the present invention.
Figure 8:
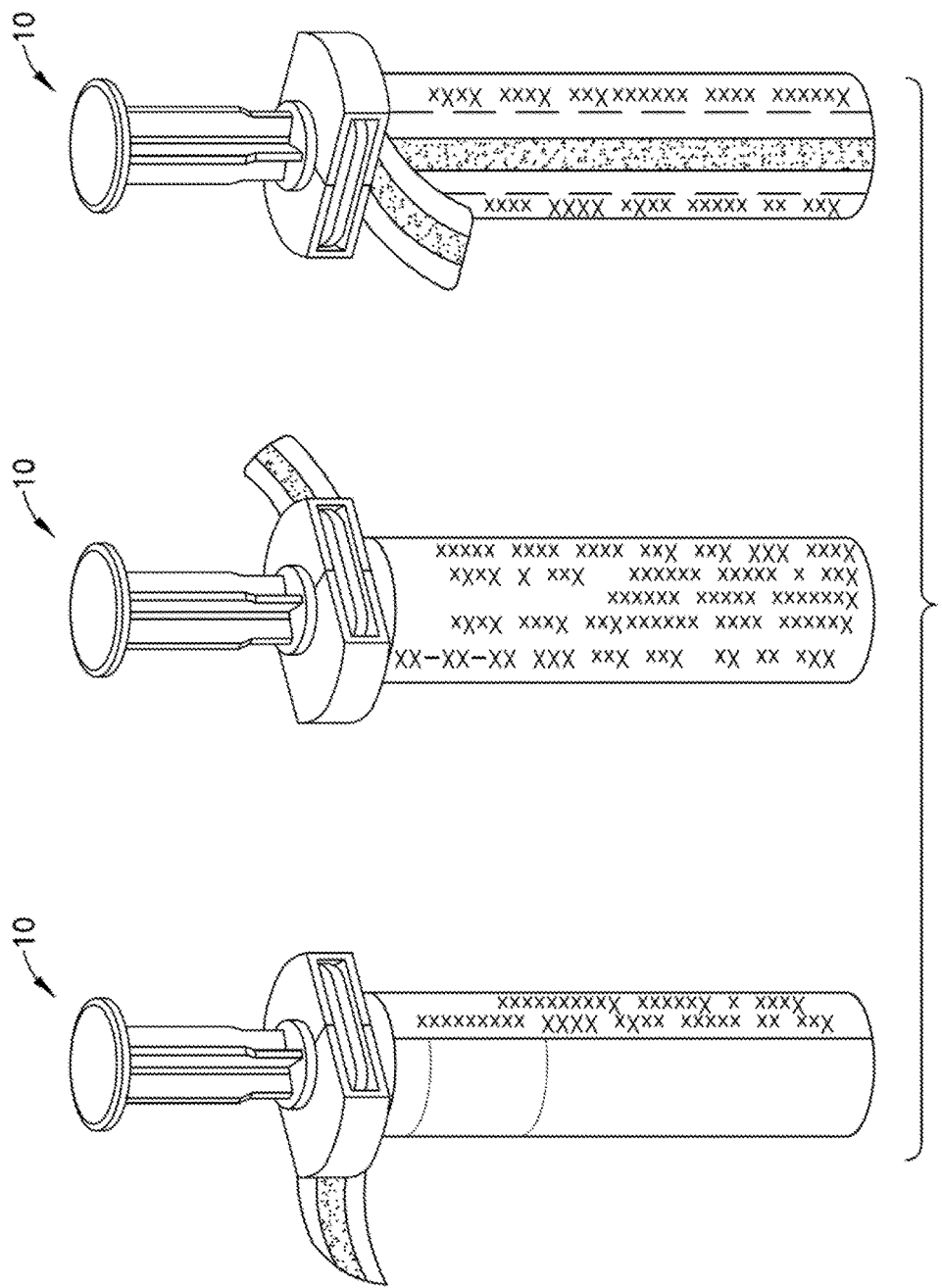
FIG. 8 is a perspective view of a plurality of syringe packaging systems in accordance with an embodiment of the present invention.
Figure 9:
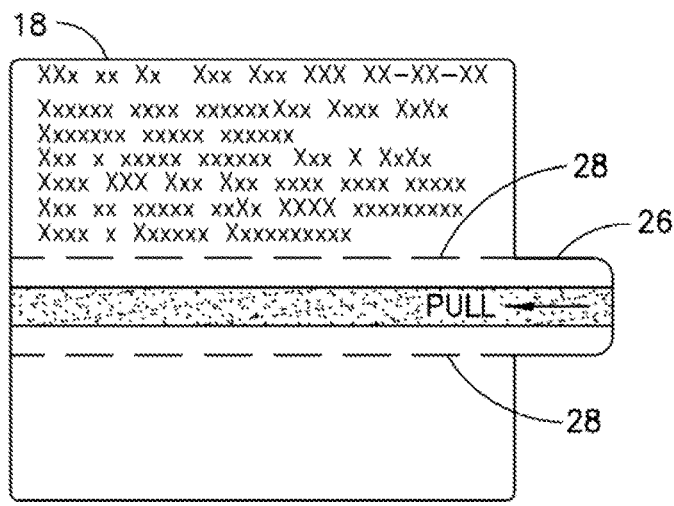
FIG. 9 is an elevation view of a label of a syringe packaging system in accordance with an embodiment of the present invention.
Figure 10:
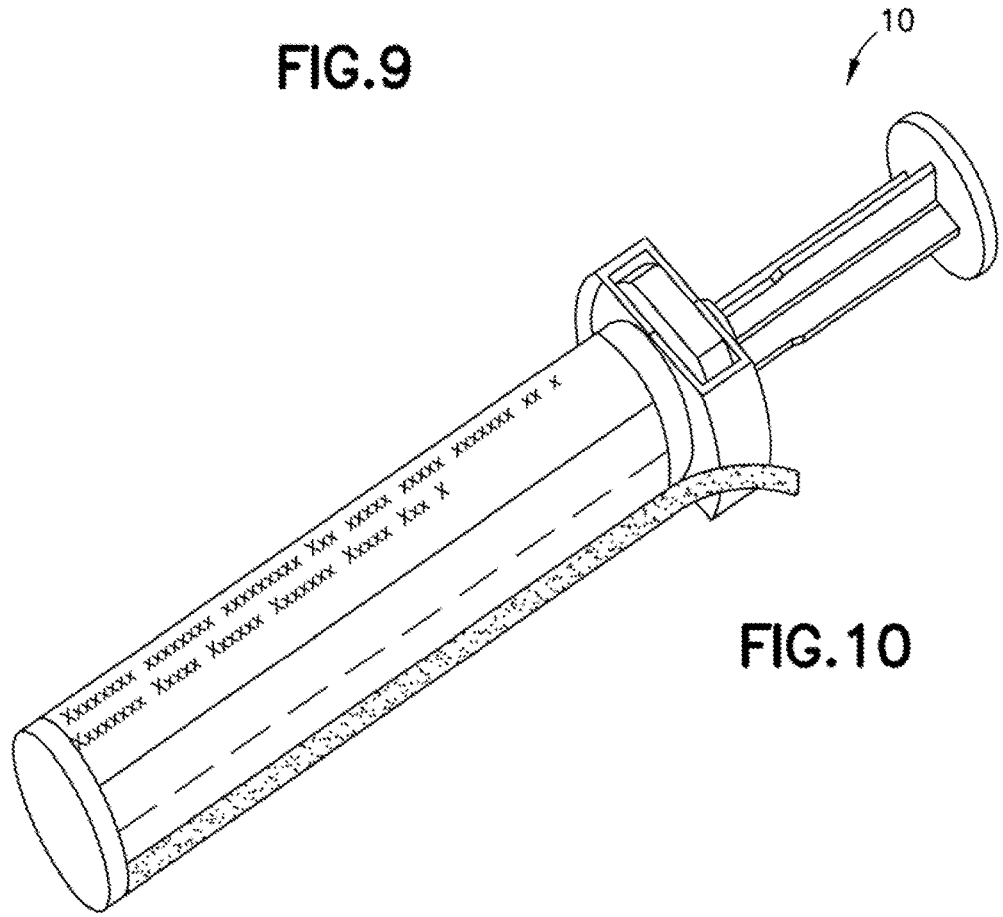
FIG. 10 is a perspective view of a syringe packaging system in accordance with an embodiment of the present invention.

Next, a plunger rod 16 of the present disclosure can be connected to the syringe 13 via engagement of the securement feature 76 of the plunger rod 16 with the engagement portion 56 of the stopper 19 as shown in FIG. 1. Referring to FIGS. 2 and 5, the syringe 13 can be loaded within the first shell portion 20 such that the disk-shaped bottom portion 124 of the first shell portion 20 shields the distal end 32 of the syringe barrel 14. Next, the first shell portion 20 and the second shell portion 22 can be engaged with the syringe 13 properly positioned within the shell 12 as shown in FIGS. 3, 6, and 13, and as described in detail above. Finally, the label 18 is securable to a portion of the first shell portion 20 and to a portion of the second shell portion 22 to connect the first shell portion 20 and the second shell portion 22 with the syringe barrel 14 enclosed within the first shell portion 20 and the second shell portion 22 as shown in FIGS. 6-12.

When a user desires to remove the syringe 13 from the shell 12, the pull tab strip 26 of the label 18 is pulled and removed. Next, the first shell portion 20 and the second shell portion 22 can be separated and the syringe 13 removed. Advantageously, the syringe 13 is ready to be administered immediately upon removal of the shell 12.

FIGS. 26-31 illustrate another exemplary embodiment of the present disclosure. Referring to FIGS. 26-31, a syringe packaging system 410 includes a shell or sleeve 412; and a syringe or a syringe assembly 413 including a syringe barrel 414, a plunger rod 416, and a stopper 419. The shell 412 of the syringe packaging system 410 provides a packaging member for a pre-filled syringe, such as syringe 413. The shell 412 of the present disclosure allows for reduced storage space of a pre-filled syringe. For example, the shell 412 allows for reduced storage space of a pre-filled syringe in an automated dispensing cabinet 300 (FIG. 25).

In one embodiment, syringe assembly 413 which includes a syringe barrel 414 and a stopper 419 may correspond to the syringe assembly 13 which includes syringe barrel 14 and stopper 19. For example, syringe assembly 413 may comprise the same components discussed above with respect to syringe assembly 13. For example, as discussed above, referring to FIG. 13, in one embodiment, syringe assembly 413 or syringe assembly 13 may include syringe barrel 14 and a stopper 19. Syringe assembly 13 may be adapted for dispensing and delivery of a fluid and/or collection of a fluid. For example, syringe assembly 13 may be used for injection or infusion of fluid such as a medication or drug into a patient. Syringe assembly 13 is contemplated for use in connection with a needle, such as by connecting syringe assembly 13 to a separate needle assembly (not shown), or alternatively for connection with an intravenous (IV) connection assembly (not shown). It can be appreciated that the present disclosure can be used with any type of syringe assembly, particularly those which are placed in a controlled storage environment in which storage space is limited. These types of syringes include traditional pre-filled syringe assemblies, metered dose syringes, aspiration syringes for withdrawing fluid from a patient or medication from a container, and the like.

In one embodiment, the shell 412 can be designed for a syringe 13 that is a cut flange syringe. In other embodiments, the shell 412 can be designed for a syringe 13 that is a round flange syringe. In other embodiments, the shell 412 can be designed for other syringes.

Referring to FIGS. 1 and 13, syringe barrel 14 generally includes a barrel body having a sidewall 30 extending between a first or distal end 32 and a second or proximal end 34. Sidewall 30 defines an elongate aperture or interior chamber 36 of syringe barrel 14. In one embodiment, interior chamber 36 may span the extent of syringe barrel 14 so that syringe barrel 14 is cannulated along its entire length. In one embodiment, syringe barrel 14 may be in the general form of an elongated cylindrical barrel as is known in the art in the general shape of a hypodermic syringe. In alternative embodiments, syringe barrel 14 may be in other forms for containing a fluid for delivery, such as in the general form of an elongated rectangular barrel, for example. Syringe barrel 14 may be formed of glass, or may be injection molded from thermoplastic material such as polypropylene and polyethylene according to techniques known to those of ordinary skill in the art, though it is to be appreciated that syringe barrel 14 may be made from other suitable materials and according to other applicable techniques. In certain configurations, syringe barrel 14 may include an outwardly extending flange 40 about at least a portion of proximal end 34. Flange 40 may be configured for easy grasping by a medical practitioner, as will be discussed herein.

Distal end 32 of syringe barrel 14 includes an outlet opening 38 (FIG. 13) which is in fluid communication with chamber 36. Outlet opening 38 may be sized and adapted for engagement with a separate device, such as a needle assembly or IV connection assembly and, therefore, may include a mechanism for such engagement as is conventionally known. For example, distal end 32 may include a generally-tapered luer tip for engagement with an optional separate tapered luer structure of such a separate device for attachment therewith (not shown). In one configuration, both the tapered luer tip and the separate tapered luer structure may be provided with the syringe assembly 13. In such a configuration, the separate tapered luer structure may be fitted with an attachment mechanism, such as a threaded engagement, for corresponding engagement with a separate device (not shown). In another configuration, the tapered luer tip may be provided for direct engagement with a separate device (not shown). In addition, a mechanism for locking engagement therebetween may also be provided with at least one of the tapered luer tip and/or the separate tapered luer structure, such as a luer collar or luer lock including interior threads. Such luer connections and luer locking mechanisms are well known in the art.

Proximal end 34 of syringe barrel 14 is generally open-ended, but is intended to be closed off to the external environment as discussed herein. Syringe barrel 14 may also include markings, such as graduations located on sidewall 30, for providing an indication as to the level or amount of fluid contained within interior chamber 36 of syringe barrel 14. Such markings may be provided on an external surface of sidewall 30, an internal surface of sidewall 30, or integrally formed or otherwise within sidewall 30 of syringe barrel 14. In other embodiments, alternatively, or in addition thereto, the markings may also provide a description of the contents of the syringe or other identifying information as may be known in the art, such as maximum and/or minimum fill lines.

Syringe barrel 14 may be useful as a pre-filled syringe, and, therefore, may be provided for end use with a fluid F (FIG. 13), such as a medication or drug, contained within interior chamber 36 of syringe barrel 14, pre-filled by the manufacturer. In this manner, syringe barrel 14 can be manufactured, pre-filled with a medication, sterilized, and packaged in appropriate packaging such as shell 12 for delivery, storage, and use by the end user, without the need for the end user to fill the syringe with medication from a separate vial prior to use. In one embodiment, syringe barrel 14 may include a tip cap or sealing cap member 42 including a seal 44 disposed at distal end 32 of syringe barrel 14 to seal a fluid F, such as a medication, within interior chamber 36 of syringe barrel 14. In one embodiment, seal 44 may be formed of a pierceable elastomer material.

As used herein, the term "drug" and/or "medication" refers to a pharmaceutically active ingredient(s) and any pharmaceutical liquid composition containing the pharmaceutically active ingredient(s). Pharmaceutical liquid compositions include forms such as solutions, suspensions, emulsions, and the like. These pharmaceutical liquid compositions can be administered orally or by injection.

Referring to FIG. 13, syringe assembly 413 or syringe assembly 13 includes stopper 19 which is moveably or slidably disposed within interior chamber 36 of syringe barrel 14, and in sealing contact with the internal surface of sidewall 30 of syringe barrel 14. Stopper 19 is sized relative to syringe barrel 14 to provide sealing engagement with the interior surface of sidewall 30 of syringe barrel 14. Additionally, stopper 19 may include one or more annular ribs extending around the periphery of stopper 19 to increase the sealing engagement between stopper 19 and the interior surface of sidewall 30 of syringe barrel 14. In alternate embodiments, a singular O-ring or a plurality of O-rings may be circumferentially disposed about stopper 19 to increase the sealing engagement with the interior surface of sidewall 30 of syringe barrel 14.

Referring to FIG. 13, in one embodiment, stopper 19 includes a first or distal end 50 and a second or proximal end 52 defining a plunger receiving aperture 54 formed therein and having a securement feature or engagement portion 56 for securing plunger rod 16 to stopper 19. In one embodiment, referring to FIG. 13, the engagement portion 56 may include a threaded portion 58.

Figure 26:
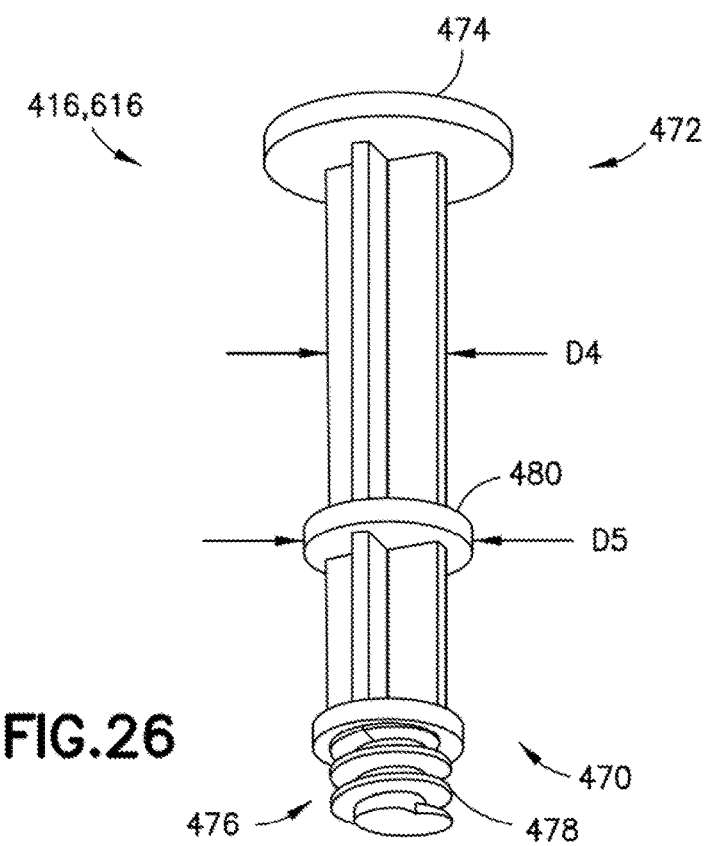
FIG. 26 is a perspective view of a plunger rod in accordance with another embodiment of the present invention.
Figure 27:
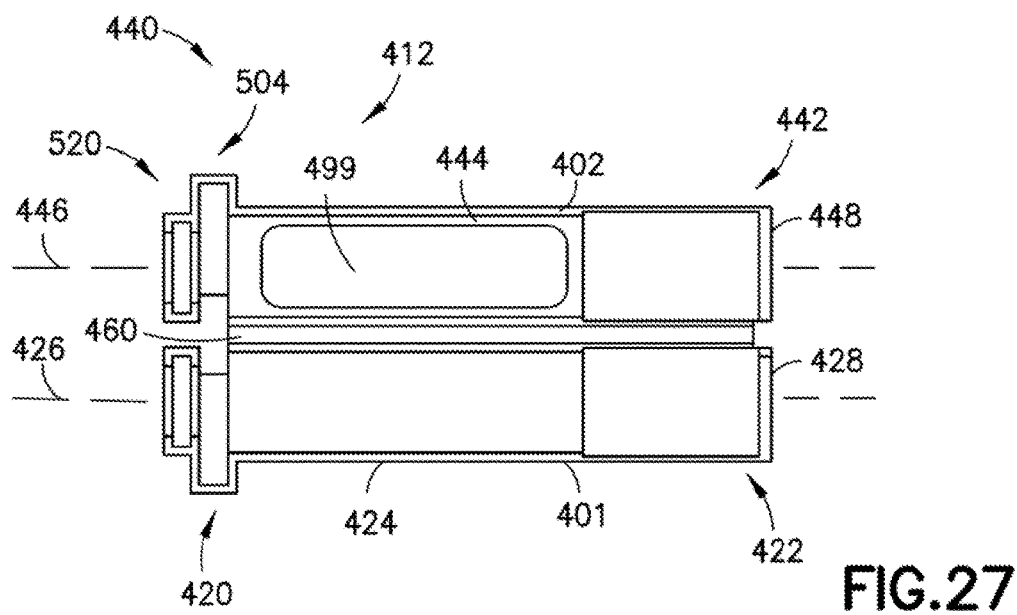
FIG. 27 is a perspective view of a shell in accordance with another embodiment of the present invention.

Referring to FIG. 26, syringe assembly 413 further includes plunger rod 416 which provides a mechanism for dispensing fluid contained within interior chamber 36 of syringe barrel 14 through outlet opening 38 upon connection of plunger rod 416 to syringe barrel 14 via stopper 19 as described in detail above with respect to plunger rod 16 and syringe barrel 14. Plunger rod 416 is adapted for advancing stopper 419 or stopper 19.

Referring to FIG. 26, in one embodiment, plunger rod 416 is sized for movement within interior chamber 36 of syringe barrel 14 as discussed above, and generally includes a first or distal end 470, a second or proximal end 472, a flange 474 disposed adjacent second end 472, a securement feature or engagement portion 476 for securing plunger rod 416 to stopper 419 or stopper 19, and a disk 480. In one embodiment, referring to FIG. 26, the engagement portion 476 of plunger rod 416 may include a threaded portion 478. In one embodiment, the flange 474 forms a thumb pad for a user to manipulate the plunger rod 416. In one embodiment, the engagement portion 476 is disposed adjacent the first end 470.

In one embodiment, plunger rod 416 can be secured to stopper 19 by threadingly engaging threaded portion 58 of stopper 19 to threaded portion 478 of plunger rod 416 as shown in FIG. 13. In other embodiments, plunger rod 416 can be secured to stopper 419 or stopper 19 using a snap fit mechanism, a ball detent, locking tabs, spring loaded locking mechanism, latch, adhesive, or other similar mechanism. In all embodiments, plunger rod 416 is locked, secured, or engaged to stopper 19, i.e., significant relative movement between plunger rod 416 and stopper 19 is limited and/or prevented.

In some embodiments, plunger rod 416 and stopper 19 may be co-formed such as by co-extrusion. In other embodiments, plunger rod 416 and stopper 19 may be integrally formed as a plunger/stopper assembly.

Figure 28:
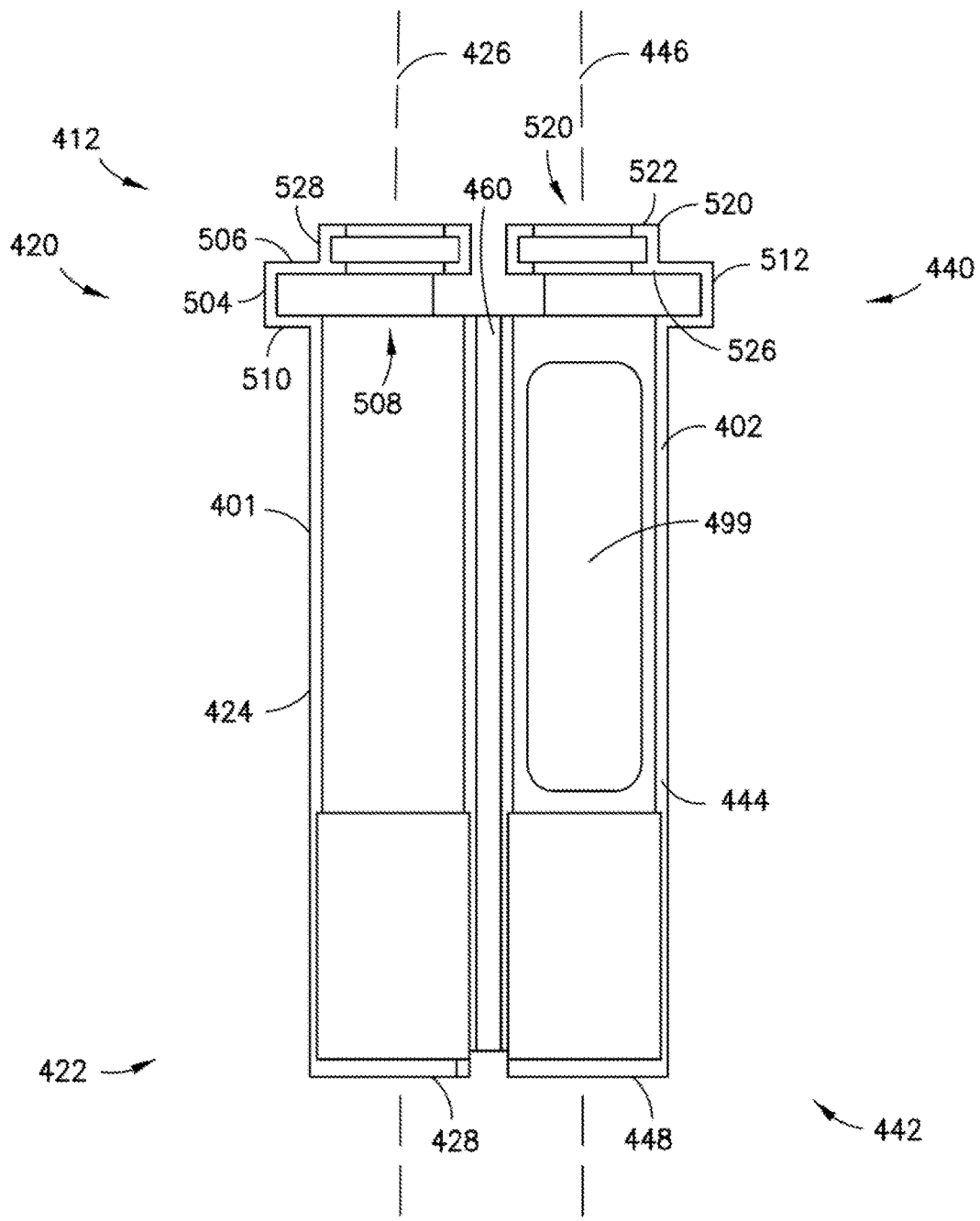
FIG. 28 is a perspective view of a first step of using a shell of the present disclosure in accordance with an embodiment of the present invention
Figure 29:
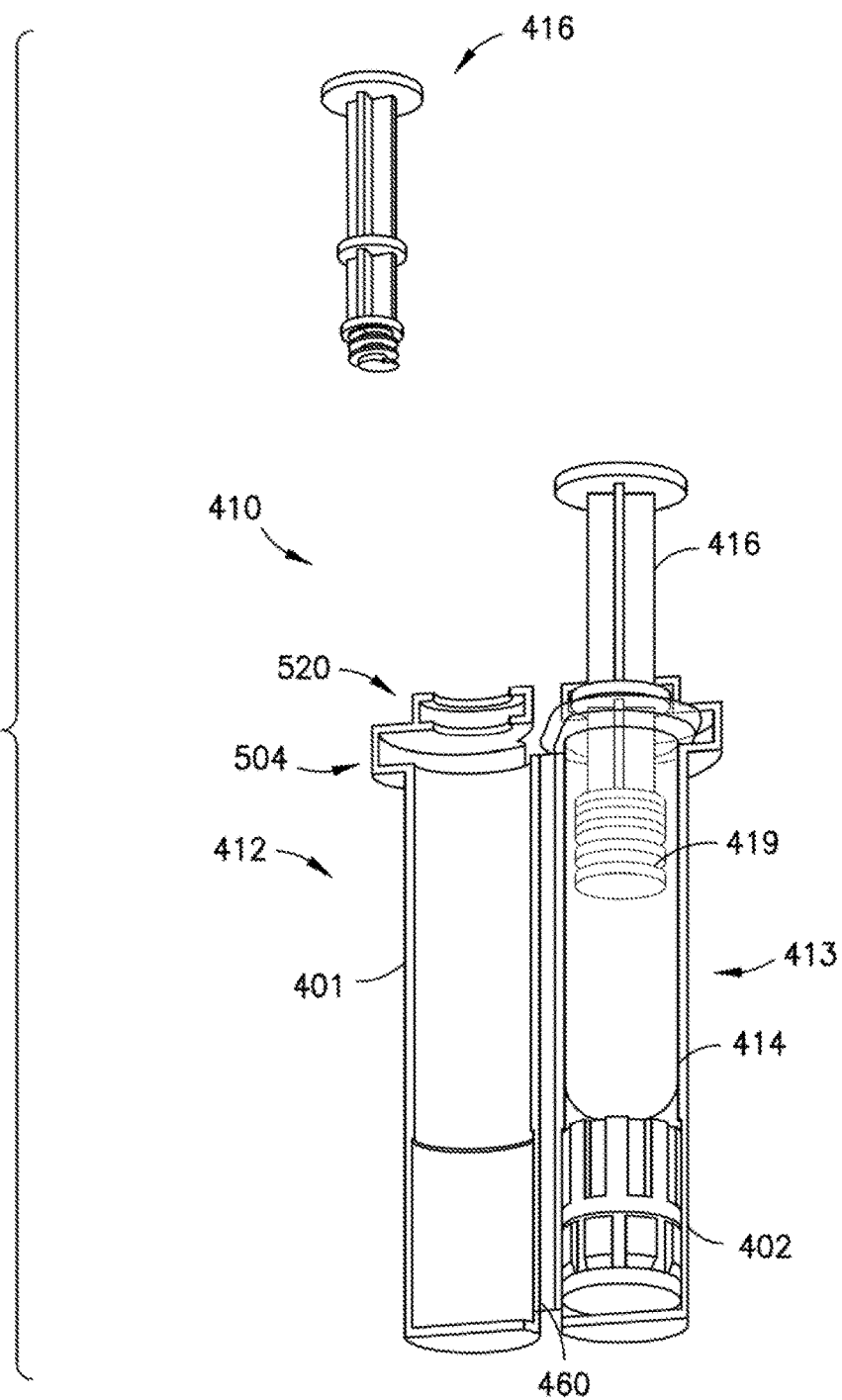
FIG. 29 is a perspective view of a second step of using a shell of the present disclosure in accordance with an embodiment of the present invention.
Figures 30, 31:
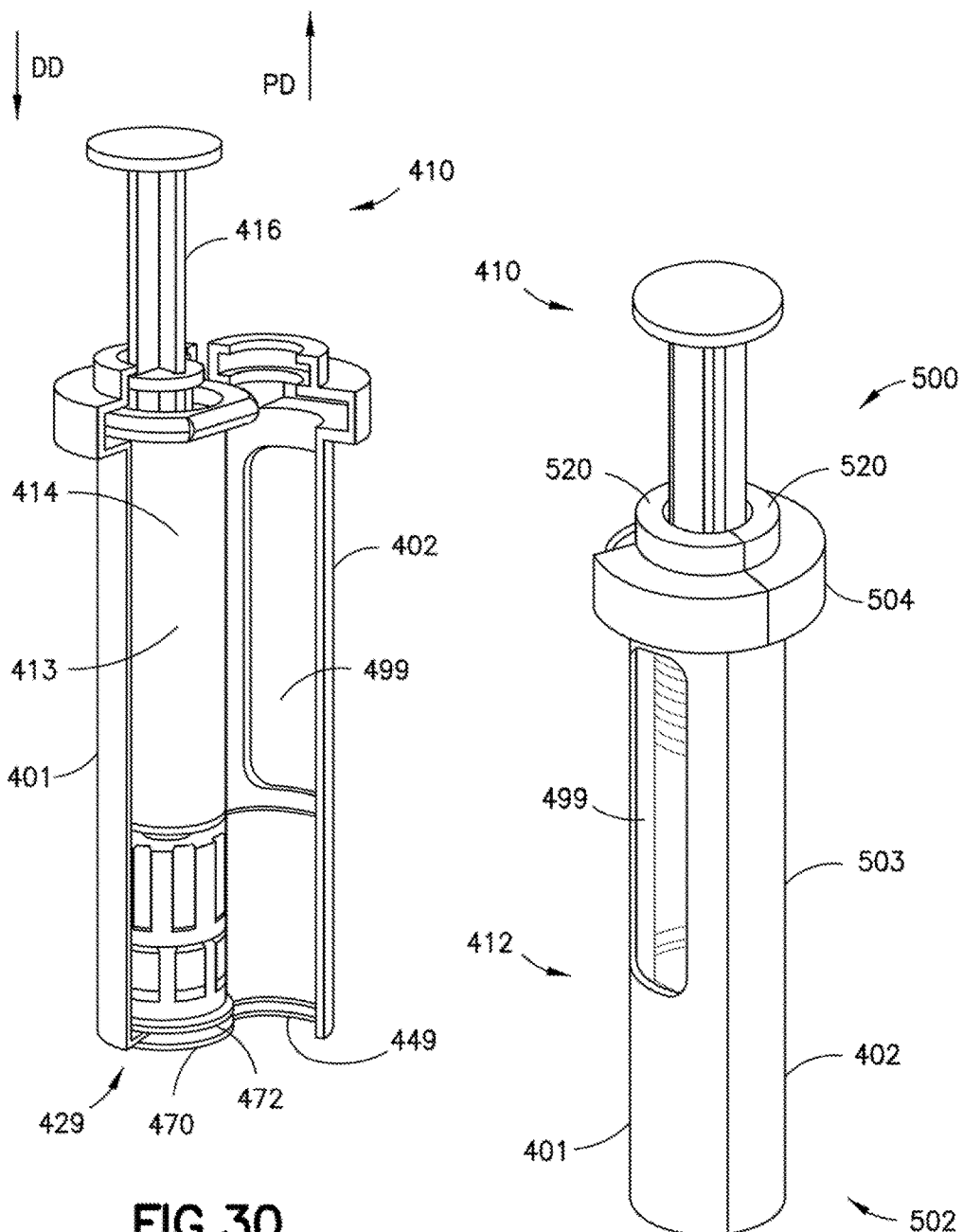
FIG. 30 is a perspective view of a third step of using a shell of the present disclosure in accordance with an embodiment of the present invention.
FIG. 31 is a perspective view of a fourth step of using a shell of the present disclosure in accordance with an embodiment of the present invention.
Figure 32:
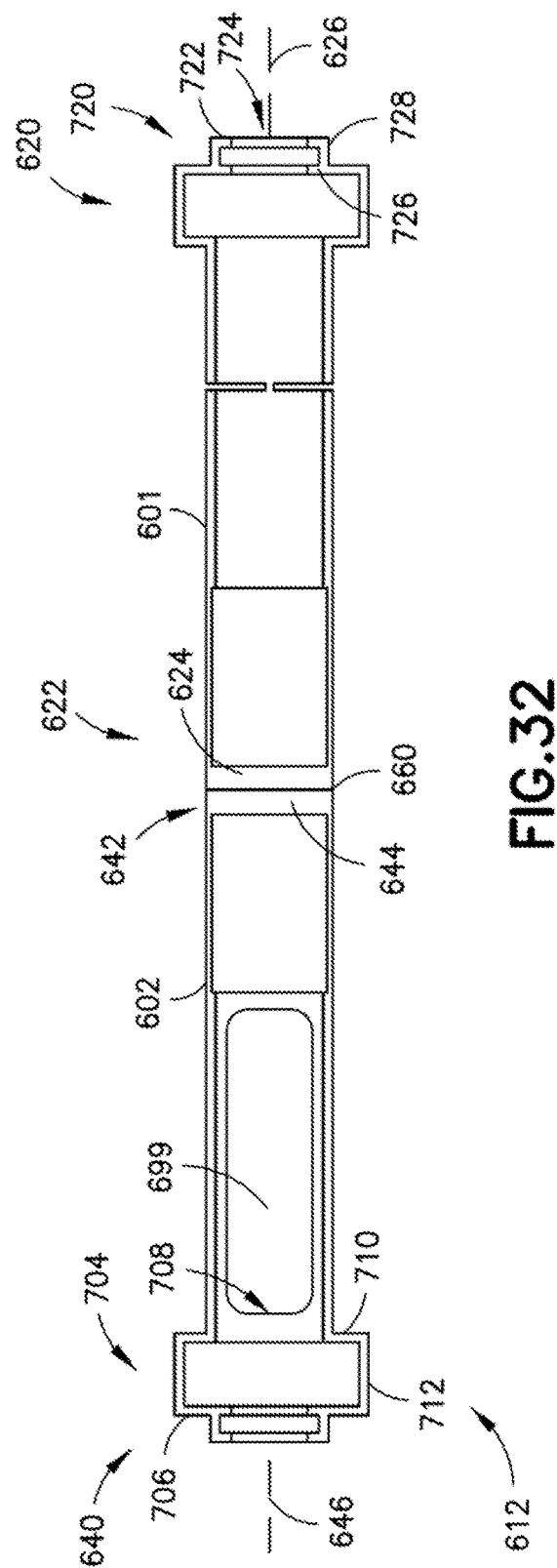
FIG. 32 is a perspective view of a shell in accordance with another embodiment of the present invention.

Referring to FIGS. 26-31, the plunger rod 416 includes a disk 480. Referring to FIG. 26, the plunger rod 416 has a plunger rod diameter D4 and the disk 480 has a disk diameter D5. In one embodiment, the disk diameter D5 is greater than the plunger rod diameter D4. In this manner, with the syringe barrel 414 or syringe barrel 14 enclosed within the shell 412, the disk 480 of the plunger rod 416 limits and/or prevents movement of the plunger rod 416 in a distal direction DD (FIG. 30) and the disk 480 of the plunger rod 416 limits and/or prevents movement of the plunger rod 416 in a proximal direction PD (FIG. 30). For example, with the shell 412 in the closed position, contact between the plunger rod disk 480 and the plunger rod disk surrounding portion 520 limits movement of the plunger rod 416 in a distal direction DD and in a proximal direction PD. Referring to FIG. 31, with the shell 412 in the closed position, a portion of the plunger rod 416 extends from the second shell proximal aperture 524. In one embodiment, the disk 480 is disposed between the proximal end 472 of the plunger rod 416 and the distal end 470 of the plunger rod 416.

Referring to FIGS. 19 and 26, in one embodiment, the length of a plunger rod 416 of the present disclosure (FIG. 26) is shorter than the length of a conventional or standard plunger rod 200 (FIG. 19). In this manner, a plunger rod 416 of the present disclosure allows for reduced storage space of a pre-filled syringe.

Additionally, at the end of the injection, when the entire drug has been delivered, the thumb pad or flange 474 of the plunger rod 416 of the present disclosure is much closer to the flange 40 of the syringe barrel 14 than a standard syringe is. For example, in one embodiment, the distance between an upper surface of the flange 40 of the syringe barrel 14 and a lower surface of the flange 474 of the plunger rod 416 may be between 0.5 to 2.5 mm. In another embodiment, the distance between an upper surface of the flange 40 of the syringe barrel 14 and a lower surface of the flange 474 of the plunger rod 416 may be between 0.9 to 2.3 mm. In another embodiment, the distance between an upper surface of the flange 40 of the syringe barrel 14 and a lower surface of the flange 474 of the plunger rod 416 may be around 1.6 mm. In this manner, the global length of a prefilled syringe is reduced, leading to a smaller required space for storage.

With any plunger rod 416 of the present disclosure, it is possible to rotate the syringe 13 inside the shell 412 to read the information written on the syringe barrel 14 through a transparent portion of the sleeve 412, i.e., the viewing window 499 (FIG. 28), or to see the integrity of a liquid contained inside the syringe 13. In one embodiment, one of the first shell portion 401 and the second shell portion 402 include a transparent window or viewing window 499. In another embodiment, both the first shell portion 401 and the second shell portion 402 may include a transparent window or viewing window 499.

Referring to FIGS. 27-31, a shell 412 of the present disclosure encloses the syringe barrel 414 or syringe barrel 14 and includes a proximal end 500, a distal end 502, and a sidewall 503 extending therebetween. In one embodiment, the proximal end 500 includes a syringe flange surrounding portion 504 that includes a top wall 506 that defines a first shell proximal aperture 508, a bottom wall 510, and a sidewall 512 extending therebetween. The shell 412 of the present invention provides a mechanical protection of the syringe 13 that is contained inside. The shell 412 also provides a good support for labeling as described above. In one embodiment, the thickness of the sidewall 503 of the shell 412 may be between 0.5 mm and 1 mm.

In one embodiment, the proximal end 500 also includes a plunger rod disk surrounding portion 520 that includes a top wall 522 that defines a second shell proximal aperture 524, a bottom wall 526, and a sidewall 528 extending therebetween.

Referring to FIGS. 27-31, in one embodiment, a shell 412 of the present disclosure includes a first shell portion 401 and a second shell portion 402 for enclosing the syringe barrel 414 as shown in FIG. 31. The first shell portion 401 includes a proximal end 420, a distal end 422, and a first sidewall 424. The second shell portion 402 includes a proximal end 440, a distal end 442, and a second sidewall 444.

Referring to FIGS. 27-31, the shell 412 also includes a hinge 460 connected to a portion of the first sidewall 424 of the first shell portion 401 and a portion of the second sidewall 444 of the second shell portion 402. In one embodiment, the hinge 460 connects the first shell portion 401 and the second shell portion 402 together such that the shell 412 is transitionable between an open position (FIGS. 28 and 29) and a closed position (FIG. 31) in which the syringe barrel 414 is enclosed within the first shell portion 401 and the second shell portion 402.

In one embodiment, the hinge 460 connects the two parts, e.g., the first and second shell portions 401, 402, thereby forming a single piece, e.g., the shell 412, that is able to protect the syringe 413.

Referring to FIG. 28, with the shell 412 in the open position, a longitudinal axis 426 of the first shell portion 401 is parallel to a longitudinal axis 446 of the second shell portion 402.

Referring to FIG. 31, with the shell 412 in the closed position, the first shell portion 401 and the second shell portion 402 together define a syringe flange surrounding portion 504 having a top wall 506 that defines a first shell proximal aperture 508, a bottom wall 510, and a sidewall 512 extending therebetween. With the shell 412 in the closed position, the syringe flange surrounding portion 504 encloses the flange 40 of the syringe barrel 414 therein. In one embodiment, the syringe flange surrounding portion 504 is disposed adjacent the proximal end 420 of the first shell portion 401 and the proximal end 440 of the second shell portion 402.

Referring to FIG. 31, with the shell 412 in the closed position, the first shell portion 401 and the second shell portion 402 together define a plunger rod disk surrounding portion 520 having a top wall 522 that defines a second shell proximal aperture 524, a bottom wall 526, and a sidewall 528 extending therebetween. With the shell 412 in the closed position, the plunger rod disk surrounding portion 520 encloses the plunger rod disk 480 therein.

In one embodiment, shell 412, e.g., first shell portion 401 and second shell portion 402, is formed of a plastic material. For example, shell 412, e.g., first shell portion 401 and second shell portion 402, may be formed of polyethylene terephthalate (PET), polypropylene (PP), polycarbonate (PC), or other material. In one embodiment, a portion of shell 412, e.g., first shell portion 401 and second shell portion 402, is formed of a transparent material. In this manner, referring to FIGS. 28-31, a portion of the shell 412 forms a viewing window 499 that allows a user to see data and/or information written on an outer surface of the syringe barrel 414.

The first shell portion 401 and the second shell portion 402 are each designed so that when they are assembled together they form a global tube or shell 412 to receive a pre-filled syringe 413. In one embodiment, the distal end 422 of the first shell portion 401 includes a first bottom wall 428 and the distal end 442 of the second shell portion 402 includes a second bottom wall 448. With the shell 412 in the closed position, the first bottom wall 428 overlaps the second bottom wall 448. With the shell 412 in the closed position, the overlapping first and second bottom walls 428, 448 shield the distal end 32 of the syringe barrel 14.

In such an embodiment, the bottom walls 428, 448 act as a barrier to avoid any piercing and/or withdrawal of a drug contained inside the syringe 413 through a seal 44 of the pre-filled syringe 413, with a needle, for example. In this manner, with the syringe barrel 414 enclosed within the shell 412, the bottom walls 428, 448 shield the distal end 32 and the seal 44 of the syringe barrel 414. The shell 412 prevents any piercing of the syringe barrel 414 and avoids any withdrawal of a drug contained inside the syringe barrel 414.

In another embodiment, the first shell portion 401 includes a distal end 422 having a disk-shaped bottom portion 429. In another embodiment, the second shell portion 402 includes a distal end 442 defining an open bottom 449. In such an embodiment, with the first shell portion 401 engaged with the second shell portion 402 to form the shell 412, the disk-shaped bottom portion 429 of the first shell portion 401 closes the open bottom 449 of the second shell portion 402.

In this particular configuration, the distal end 422 of the first shell portion 401 has a bottom in the form of a disk, i.e., the disk-shaped bottom portion 429, which matches the open bottom 449 of the distal end 442 of the second shell portion 402. In such an embodiment, the disk-shaped bottom portion 429 acts as a barrier to avoid any piercing and/or withdrawal of a drug contained inside the syringe 13 through a seal 44 of the pre-filled syringe 13, with a needle, for example. In this manner, with the syringe barrel 14 enclosed within the shell 412, the disk-shaped bottom portion 429 of the first shell portion 401 shields the distal end 422 and the seal 44 of the syringe barrel 14. The shell 412 prevents any piercing of the syringe barrel 14 and avoids any withdrawal of a drug contained inside the syringe barrel 14.

In another embodiment, the distal end 422 of the first shell portion 401 and the distal end 442 of the second shell portion 402 could have identical half-disk shaped bottom portions.

In another embodiment, the distal end 422 of the first shell portion 401 has a half-disk bottom portion with a thickness t and the distal end 442 of the second shell portion 402 has a full-disk with a step in thickness. For example, the thinner portion could have a thickness t' while the thicker portion could have a thickness that corresponds to the global thickness t+t'. In this configuration, no needle access to a drug contained inside the syringe 13 through a seal 44 of the pre-filled syringe 13 is allowed. In one embodiment, the thickness of the bottom portion of the shell 412 is at least 1 mm. In another embodiment, the thickness of the bottom portion of the shell 412 is between 1 mm and 1.2 mm.

In another embodiment, referring to FIG. 30, the first shell portion 401 includes a first bottom wall 470 and a second bottom wall 472. In this manner, with the syringe barrel 14 enclosed within the shell 412, the bottom walls 470, 472 shield the distal end 422 and the seal 44 of the syringe barrel 14. The shell 412 prevents any piercing of the syringe barrel 14 and avoids any withdrawal of a drug contained inside the syringe barrel 14.

Referring to FIGS. 27-31, the interaction between the syringe flange surrounding portion 504 and the flange 40 of the syringe barrel 414 will now be described.

In one embodiment, as described above, the proximal end 500 of shell 412 includes a syringe flange surrounding portion 504 that includes a top wall 506 that defines a first shell proximal aperture 508, a bottom wall 510, and a sidewall 512 extending therebetween.

Referring to FIGS. 27-31, with the syringe barrel 414 enclosed within the shell 412, the syringe flange surrounding portion 504 encloses the flange 40 of the syringe barrel 414 therein. In such an embodiment, the flange 40 of the syringe barrel 414 is contained inside the surrounding syringe flange surrounding portion 504 of the shell 412 leading to mechanical retention of the syringe barrel 414. In one embodiment, the thickness of the syringe flange surrounding portion 504 is an important design parameter as no deformation of the surrounding syringe flange surrounding portion 504 is allowed to avoid syringe barrel 414 withdrawal. In one embodiment, the thickness of the walls of the syringe flange surrounding portion 504 are at least 1 mm.

Referring to FIGS. 27-31, the interaction between the plunger rod disk surrounding portion 520 and the disk 480 of the plunger rod 416 will now be described.

In one embodiment, as described above, the proximal end 500 also includes a plunger rod disk surrounding portion 520 that includes a top wall 522 that defines a second shell proximal aperture 524, a bottom wall 526, and a sidewall 528 extending therebetween.

Referring to FIGS. 27-31, with the syringe barrel 414 enclosed within the shell 412, the plunger rod disk surrounding portion 520 encloses the disk 480 of the plunger rod 416 therein. In such an embodiment, the disk 480 is contained inside the surrounding plunger rod disk surrounding portion 520 of the shell 412 leading to mechanical retention of the plunger rod 416. In one embodiment, the thickness of the plunger rod disk surrounding portion 520 is an important design parameter as no deformation of the surrounding plunger rod disk surrounding portion 520 is allowed to avoid plunger rod 416 withdrawal. In one embodiment, the thickness of the walls of the syringe flange surrounding portion 504 are at least 1 mm.

Referring to FIGS. 26-31, the plunger rod 416 includes a disk 480. Referring to FIG. 26, the plunger rod 416 has a plunger rod diameter D4 and the disk 480 has a disk diameter D5. In one embodiment, the disk diameter D5 is greater than the plunger rod diameter D4. In this manner, with the syringe barrel 414 or syringe barrel 14 enclosed within the shell 412, the disk 480 of the plunger rod 416 limits and/or prevents movement of the plunger rod 416 in a distal direction DD (FIG. 30) and the disk 480 of the plunger rod 416 limits and/or prevents movement of the plunger rod 416 in a proximal direction PD (FIG. 30). For example, with the shell 412 in the closed position, contact between the plunger rod disk 480 and the plunger rod disk surrounding portion 520 limits movement of the plunger rod 416 in a distal direction DD and in a proximal direction PD. Referring to FIG. 31, with the shell 412 in the closed position, a portion of the plunger rod 416 extends from the second shell proximal aperture 524. In one embodiment, the disk 480 is disposed between the proximal end 472 of the plunger rod 416 and the distal end 470 of the plunger rod 416.

With the syringe barrel 414 enclosed within the shell 412, a portion of the plunger rod 416 extends from the second shell proximal aperture 524. The second shell proximal aperture 524 only allows passage of a portion of the plunger rod 416. The syringe flange surrounding portion 504 and the plunger rod disk surrounding portion 520 act as a barrier to avoid any piercing and/or withdrawal of a drug contained inside the syringe 413 through a stopper 19 of the pre-filled syringe 413, with a needle, for example. In this manner, with the syringe barrel 414 enclosed within the shell 412, the syringe flange surrounding portion 504 and the plunger rod disk surrounding portion 520 of the shell 412 shield the syringe barrel 414. The shell 412 prevents any piercing of the syringe barrel 14 and stopper 19 and avoids any withdrawal of a drug contained inside the syringe barrel 14.

Referring to FIGS. 27-31, with the syringe barrel 414 enclosed within the shell 412, the plunger rod disk surrounding portion 520 encloses the disk 480 of the plunger rod 416 therein.

In this manner, the disk 480 enclosed within the plunger rod disk surrounding portion 520 prevents movement of the plunger rod 416 in a distal direction DD thereby preventing any leakage that should occur when high pressures are applied on the plunger rod 416 leading to sterility breakage.

The disk 480 enclosed within the plunger rod disk surrounding portion 520 prevents movement of the plunger rod 416 in a proximal direction PD and provides three different functions. First, this configuration avoids the withdrawal of the plunger rod 416 from the shell 412. Second, this configuration provides tamper evidence feature as the disk 480 of the plunger rod 416 ensures that the plunger rod 416 cannot be replaced if it has been removed. Also, the disk 480 of the plunger rod 416 guarantees the sterility of the product as it limits the displacement of the stopper 19 during transportation, e.g., the remaining bubble always present inside the container can be put under pressure during air transportation and lead to sterility loss.

Additionally, referring to FIGS. 27-31, with the syringe 413 enclosed within the shell 412, the first shell proximal aperture 508 and the second shell proximal aperture 524 have specific diameters to allow for the free rotation of the plunger rod 416 and the syringe 413. In this manner, for example, when a nurse wants to control the integrity of the product and read information present on a label affixed to a surface of the syringe barrel 14, she will be able to rotate the syringe 413 by rotating the plunger rod 416. Additionally, the syringe flange surrounding portion 504 is sized to minimize storage space but provide flange protection to the flange 40 of the syringe barrel 14 and to prevent any flange breakage.

Referring to FIGS. 29-31, the disk 480 is sized to contact the walls 522, 526 of the plunger rod disk surrounding portion 520, with the syringe barrel 14 enclosed within the shell 412, to prevent movement of the plunger rod 416 in a distal direction DD and a proximal direction PD, as described above. Also, the disk 480 is sized such that with the syringe barrel 14 removed from the shell 412, the plunger rod 416 is adapted to advance stopper 19 and plunger rod 416 is sized for movement within interior chamber 36 of syringe barrel 14, i.e., the disk 480 can slide within the syringe barrel 14.

Referring to FIGS. 28-31, packaging of a syringe 413 within shell 412 will now be described. Initially, syringe barrel 414, plunger rod 416, and shell 412 are sterilized according to techniques known to those of ordinary skill in the art. In some embodiments, syringe barrel 414 may be pre-filled as described above.

Next, a plunger rod 416 of the present disclosure can be connected to the syringe 413 via engagement of the securement feature 476 of the plunger rod 416 with the engagement portion 56 of the stopper 19 as shown in FIG. 1. Referring to FIGS. 29 and 30, the syringe 413 can be loaded within one of the shell portions 401, 402 such that the flange 40 of the syringe barrel 414 is received within the syringe flange surrounding portion 504 and the disk 480 of the plunger rod 416 is received within the plunger rod disk surrounding portion 520. Next, the first shell portion 401 and the second shell portion 402 can be engaged and moved to the closed position via the hinge 460 with the syringe 413 properly positioned within the shell 412 as shown in FIGS. 29-31.

When a user desires to remove the syringe 413 from the shell 412, a pull tab strip 497 of a clear shrink band 495 (FIGS. 38 and 39) is pulled and removed. Next, the first shell portion 401 and the second shell portion 402 can be separated and the syringe 413 removed. Advantageously, the syringe 413 is ready to be administered immediately upon removal of the shell 412.

FIGS. 32-36 illustrate another exemplary embodiment of the present disclosure. Referring to FIGS. 32-36, a syringe packaging system 610 includes a shell or sleeve 612; and a syringe or a syringe assembly 613 including a syringe barrel 614, a plunger rod 616, and a stopper 619. The shell 612 of the syringe packaging system 610 provides a packaging member for a pre-filled syringe, such as syringe 613. The shell 612 of the present disclosure allows for reduced storage space of a pre-filled syringe. For example, the shell 612 allows for reduced storage space of a pre-filled syringe in an automated dispensing cabinet 300 (FIG. 25).

In one embodiment, syringe assembly 613 which includes a syringe barrel 614 and a stopper 619 may correspond to the syringe assembly 13 which includes syringe barrel 14 and stopper 19. For example, syringe assembly 613 may comprise the same components discussed above with respect to syringe assembly 13.

In one embodiment, the shell 612 can be designed for a syringe 13 that is a cut flange syringe. In other embodiments, the shell 612 can be designed for a syringe 13 that is a round flange syringe. In other embodiments, the shell 612 can be designed for other syringes.

Referring to FIG. 26, syringe assembly 613 further includes plunger rod 616 which provides a mechanism for dispensing fluid contained within interior chamber 36 of syringe barrel 14 through outlet opening 38 upon connection of plunger rod 616 to syringe barrel 14 via stopper 19 as described in detail above with respect to plunger rod 16 and syringe barrel 14. Plunger rod 616 is adapted for advancing stopper 619 or stopper 19.

Referring to FIG. 26, in one embodiment, plunger rod 616 is sized for movement within interior chamber 36 of syringe barrel 14 as discussed above, and generally includes a first or distal end 470, a second or proximal end 472, a flange 474 disposed adjacent second end 472, a securement feature or engagement portion 476 for securing plunger rod 616 to stopper 619 or stopper 19, and a disk 480. In one embodiment, referring to FIG. 26, the engagement portion 476 of plunger rod 616 may include a threaded portion 478. In one embodiment, the flange 474 forms a thumb pad for a user to manipulate the plunger rod 616. In one embodiment, the engagement portion 476 is disposed adjacent the first end 470.

In one embodiment, plunger rod 616 can be secured to stopper 19 by threadingly engaging threaded portion 58 of stopper 19 to threaded portion 478 of plunger rod 616 as shown in FIG. 13. In other embodiments, plunger rod 616 can be secured to stopper 619 or stopper 19 using a snap fit mechanism, a ball detent, locking tabs, spring loaded locking mechanism, latch, adhesive, or other similar mechanism. In all embodiments, plunger rod 616 is locked, secured, or engaged to stopper 19, i.e., significant relative movement between plunger rod 616 and stopper 19 is limited and/or prevented.

In some embodiments, plunger rod 616 and stopper 19 may be co-formed such as by co-extrusion. In other embodiments, plunger rod 616 and stopper 19 may be integrally formed as a plunger/stopper assembly.

Figures 35, 36:
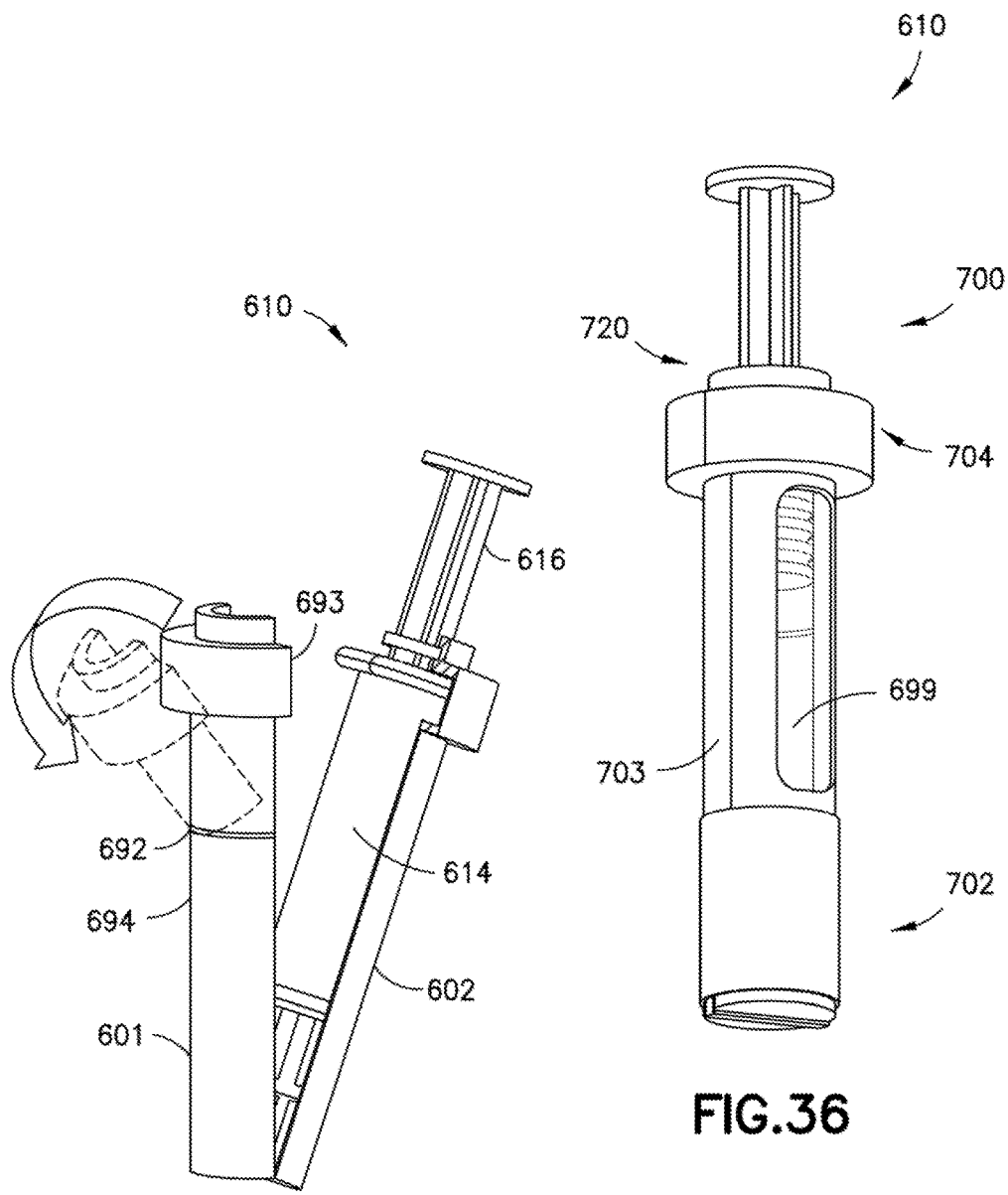
FIG. 35 is a perspective view of a third step of using a shell of the present disclosure in accordance with an embodiment of the present invention.
FIG. 36 is a perspective view of a fourth step of using a shell of the present disclosure in accordance with an embodiment of the present invention.

Referring to FIG. 26, the plunger rod 616 includes a disk 480. Referring to FIG. 26, the plunger rod 616 has a plunger rod diameter D4 and the disk 480 has a disk diameter D5. In one embodiment, the disk diameter D5 is greater than the plunger rod diameter D4. In this manner, with the syringe barrel 614 or syringe barrel 14 enclosed within the shell 612, the disk 480 of the plunger rod 616 limits and/or prevents movement of the plunger rod 616 in a distal direction DD (FIG. 36) and the disk 480 of the plunger rod 616 limits and/or prevents movement of the plunger rod 616 in a proximal direction PD (FIG. 36). For example, with the shell 612 in the closed position, contact between the plunger rod disk 480 and the plunger rod disk surrounding portion 720 limits movement of the plunger rod 616 in a distal direction DD and in a proximal direction PD. Referring to FIG. 36, with the shell 612 in the closed position, a portion of the plunger rod 616 extends from the second shell proximal aperture 724. In one embodiment, the disk 480 is disposed between the proximal end 472 of the plunger rod 616 and the distal end 470 of the plunger rod 616.

Referring to FIGS. 19 and 26, in one embodiment, the length of a plunger rod 616 of the present disclosure (FIG. 26) is shorter than the length of a conventional or standard plunger rod 200 (FIG. 19). In this manner, a plunger rod 616 of the present disclosure allows for reduced storage space of a pre-filled syringe.

Additionally, at the end of the injection, when the entire drug has been delivered, the thumb pad or flange 474 of the plunger rod 616 of the present disclosure is much closer to the flange 40 of the syringe barrel 14 than a standard syringe is. For example, in one embodiment, the distance between an upper surface of the flange 40 of the syringe barrel 14 and a lower surface of the flange 474 of the plunger rod 616 may be between 0.5 to 2.5 mm. In another embodiment, the distance between an upper surface of the flange 40 of the syringe barrel 14 and a lower surface of the flange 474 of the plunger rod 616 may be between 0.9 to 2.3 mm. In another embodiment, the distance between an upper surface of the flange 40 of the syringe barrel 14 and a lower surface of the flange 474 of the plunger rod 616 may be around 1.6 mm. In this manner, the global length of a prefilled syringe is reduced, leading to a smaller required space for storage.

With any plunger rod 616 of the present disclosure, it is possible to rotate the syringe 13 inside the shell 612 to read the information written on the syringe barrel 14 through a transparent portion of the sleeve 612, i.e., the viewing window 699 (FIG. 33), or to see the integrity of a liquid contained inside the syringe 13. In one embodiment, one of the first shell portion 601 and the second shell portion 602 include a transparent window or viewing window 699. In another embodiment, both the first shell portion 601 and the second shell portion 602 may include a transparent window or viewing window 699.

Referring to FIGS. 32-36, a shell 612 of the present disclosure encloses the syringe barrel 614 or syringe barrel 14 and includes a proximal end 700, a distal end 702, and a sidewall 703 extending therebetween. In one embodiment, the proximal end 700 includes a syringe flange surrounding portion 704 that includes a top wall 706 that defines a first shell proximal aperture 708, a bottom wall 710, and a sidewall 712 extending therebetween. The shell 612 of the present invention provides a mechanical protection of the syringe 13 that is contained inside. The shell 612 also provides a good support for labeling as described above. In one embodiment, the thickness of the sidewall 703 of the shell 612 may be between 0.5 mm and 1 mm.

In one embodiment, the proximal end 700 also includes a plunger rod disk surrounding portion 720 that includes a top wall 722 that defines a second shell proximal aperture 724, a bottom wall 726, and a sidewall 728 extending therebetween.

Referring to FIGS. 32-36, in one embodiment, a shell 612 of the present disclosure includes a first shell portion 601 and a second shell portion 602 for enclosing the syringe barrel 614 as shown in FIG. 36. The first shell portion 601 includes a proximal end 620, a distal end 622, and a first bottom wall 624. The second shell portion 602 includes a proximal end 640, a distal end 642, and a second bottom wall 644.

Referring to FIGS. 32-36, the shell 612 also includes a hinge 660 connected to a portion of the first bottom wall 624 of the first shell portion 601 and a portion of the second bottom wall 644 of the second shell portion 602. In one embodiment, the hinge 660 connects the first shell portion 601 and the second shell portion 602 together such that the shell 612 is transitionable between an open position (FIGS. 33 and 34) and a closed position (FIG. 36) in which the syringe barrel 614 is enclosed within the first shell portion 601 and the second shell portion 602.

In one embodiment, the hinge 660 connects the two parts, e.g., the first and second shell portions 601, 602, thereby forming a single piece, e.g., the shell 612, that is able to protect the syringe 613.

Figures 33, 34:
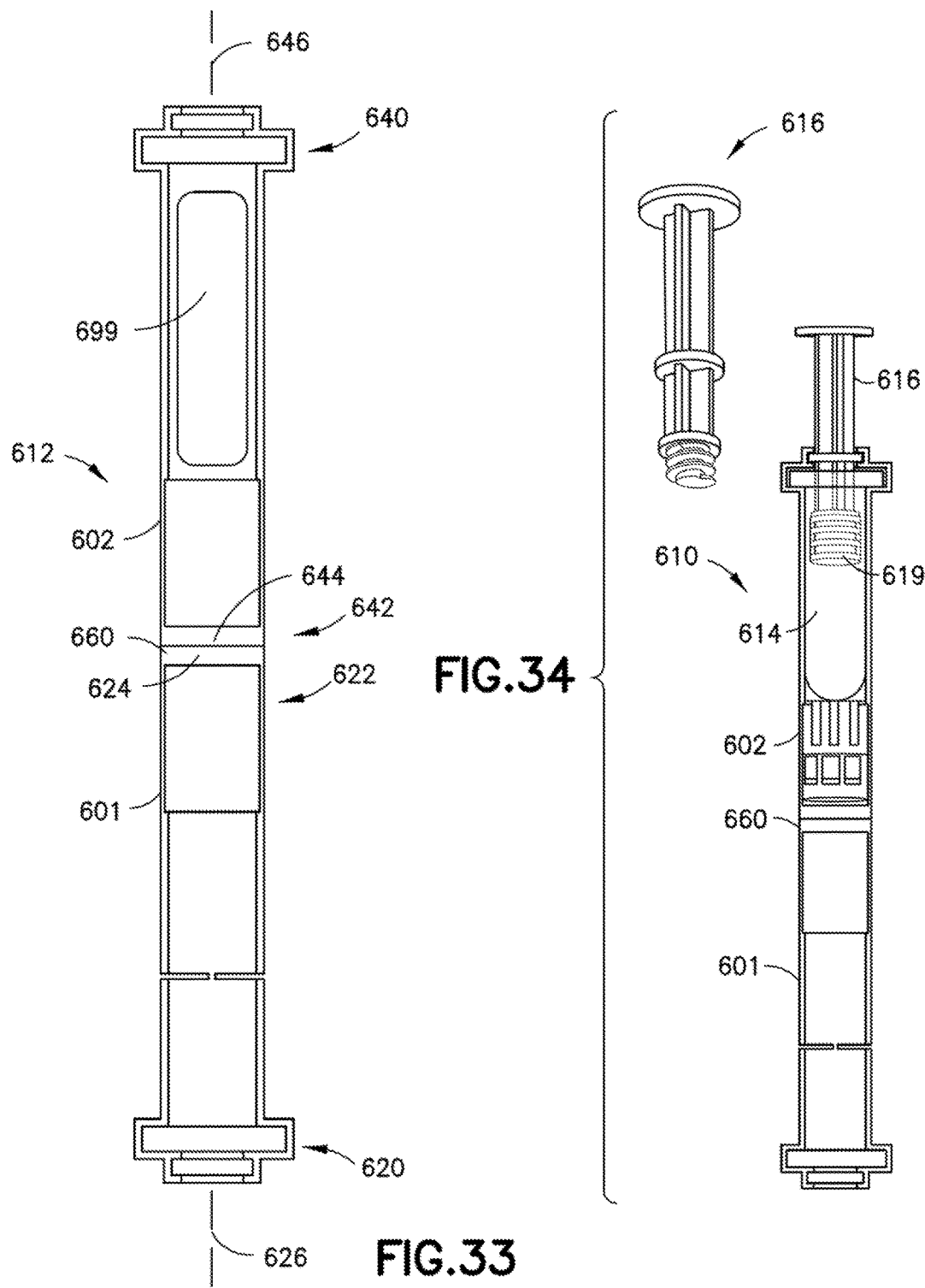
FIG. 33 is a perspective view of a first step of using a shell of the present disclosure in accordance with an embodiment of the present invention
FIG. 34 is a perspective view of a second step of using a shell of the present disclosure in accordance with an embodiment of the present invention.

Referring to FIG. 33, with the shell 612 in the open position, a longitudinal axis 626 of the first shell portion 601 and a longitudinal axis 646 of the second shell portion 602 are collinear.

In one embodiment, referring to FIG. 35, a portion of the first shell portion 601 is pivotable between a closed position and an open position. For example, referring to FIG. 35, a portion of the first shell portion 601 is pivotable between the closed position and the open position via a second hinge 692. The second hinge 692 connects an upper portion 693 of the first shell portion 601 and a lower portion 694 of the first shell portion 601.

Referring to FIG. 36, with the shell 612 in the closed position, the first shell portion 601 and the second shell portion 602 together define a syringe flange surrounding portion 704 having a top wall 706 that defines a first shell proximal aperture 708, a bottom wall 710, and a sidewall 712 extending therebetween. With the shell 612 in the closed position, the syringe flange surrounding portion 704 encloses the flange 40 of the syringe barrel 614 therein. In one embodiment, the syringe flange surrounding portion 704 is disposed adjacent the proximal end 620 of the first shell portion 601 and the proximal end 640 of the second shell portion 602.

Referring to FIG. 36, with the shell 612 in the closed position, the first shell portion 601 and the second shell portion 602 together define a plunger rod disk surrounding portion 720 having a top wall 722 that defines a second shell proximal aperture 724, a bottom wall 726, and a sidewall 728 extending therebetween. With the shell 612 in the closed position, the plunger rod disk surrounding portion 720 encloses the plunger rod disk 480 therein.

In one embodiment, shell 612, e.g., first shell portion 601 and second shell portion 602, is formed of a plastic material. For example, shell 612, e.g., first shell portion 601 and second shell portion 602, may be formed of polyethylene terephthalate (PET), polypropylene (PP), polycarbonate (PC), or other material. In one embodiment, a portion of shell 612, e.g., first shell portion 601 and second shell portion 602, is formed of a transparent material. In this manner, referring to FIGS. 33-36, a portion of the shell 612 forms a viewing window 699 that allows a user to see data and/or information written on an outer surface of the syringe barrel 614.

The first shell portion 601 and the second shell portion 602 are each designed so that when they are assembled together they form a global tube or shell 612 to receive a pre-filled syringe 613. In one embodiment, the distal end 622 of the first shell portion 601 includes a first bottom wall 624 and the distal end 642 of the second shell portion 602 includes a second bottom wall 644. With the shell 612 in the closed position, the first bottom wall 624 overlaps the second bottom wall 644. With the shell 612 in the closed position, the overlapping first and second bottom walls 624, 644 shield the distal end 32 of the syringe barrel 14.

In such an embodiment, the bottom walls 624, 644 act as a barrier to avoid any piercing and/or withdrawal of a drug contained inside the syringe 613 through a seal 44 of the pre-filled syringe 613, with a needle, for example. In this manner, with the syringe barrel 614 enclosed within the shell 612, the bottom walls 624, 644 shield the distal end 32 and the seal 44 of the syringe barrel 614. The shell 612 prevents any piercing of the syringe barrel 614 and avoids any withdrawal of a drug contained inside the syringe barrel 614.

Referring to FIGS. 33-36, the interaction between the syringe flange surrounding portion 704 and the flange 40 of the syringe barrel 614 will now be described.

In one embodiment, as described above, the proximal end 700 of shell 612 includes a syringe flange surrounding portion 704 that includes a top wall 706 that defines a first shell proximal aperture 708, a bottom wall 710, and a sidewall 712 extending therebetween.

Referring to FIGS. 33-36, with the syringe barrel 614 enclosed within the shell 612, the syringe flange surrounding portion 704 encloses the flange 40 of the syringe barrel 614 therein. In such an embodiment, the flange 40 of the syringe barrel 614 is contained inside the surrounding syringe flange surrounding portion 704 of the shell 612 leading to mechanical retention of the syringe barrel 614. In one embodiment, the thickness of the syringe flange surrounding portion 704 is an important design parameter as no deformation of the surrounding syringe flange surrounding portion 704 is allowed to avoid syringe barrel 614 withdrawal. In one embodiment, the thickness of the walls of the syringe flange surrounding portion 704 are at least 1 mm.

Referring to FIGS. 33-36, the interaction between the plunger rod disk surrounding portion 720 and the disk 480 of the plunger rod 616 will now be described.

In one embodiment, as described above, the proximal end 700 also includes a plunger rod disk surrounding portion 720 that includes a top wall 722 that defines a second shell proximal aperture 724, a bottom wall 726, and a sidewall 728 extending therebetween.

Referring to FIGS. 33-36, with the syringe barrel 614 enclosed within the shell 612, the plunger rod disk surrounding portion 720 encloses the disk 480 of the plunger rod 616 therein. In such an embodiment, the disk 480 is contained inside the surrounding plunger rod disk surrounding portion 720 of the shell 612 leading to mechanical retention of the plunger rod 616. In one embodiment, the thickness of the plunger rod disk surrounding portion 720 is an important design parameter as no deformation of the surrounding plunger rod disk surrounding portion 720 is allowed to avoid plunger rod 616 withdrawal. In one embodiment, the thickness of the walls of the syringe flange surrounding portion 704 are at least 1 mm.

Referring to FIG. 26, as described above, the plunger rod 616 includes a disk 480. Referring to FIG. 26, the plunger rod 616 has a plunger rod diameter D4 and the disk 480 has a disk diameter D5. In one embodiment, the disk diameter D5 is greater than the plunger rod diameter D4. In this manner, with the syringe barrel 614 or syringe barrel 14 enclosed within the shell 612, the disk 480 of the plunger rod 616 limits and/or prevents movement of the plunger rod 616 in a distal direction DD (FIG. 36) and the disk 480 of the plunger rod 616 limits and/or prevents movement of the plunger rod 616 in a proximal direction PD (FIG. 36). For example, with the shell 612 in the closed position, contact between the plunger rod disk 480 and the plunger rod disk surrounding portion 720 limits movement of the plunger rod 616 in a distal direction DD and in a proximal direction PD. Referring to FIG. 36, with the shell 612 in the closed position, a portion of the plunger rod 616 extends from the second shell proximal aperture 724. In one embodiment, the disk 480 is disposed between the proximal end 472 of the plunger rod 616 and the distal end 470 of the plunger rod 616.

With the syringe barrel 614 enclosed within the shell 612, a portion of the plunger rod 616 extends from the second shell proximal aperture 724. The second shell proximal aperture 724 only allows passage of a portion of the plunger rod 616. The syringe flange surrounding portion 704 and the plunger rod disk surrounding portion 720 act as a barrier to avoid any piercing and/or withdrawal of a drug contained inside the syringe 613 through a stopper 19 of the pre-filled syringe 613, with a needle, for example. In this manner, with the syringe barrel 614 enclosed within the shell 612, the syringe flange surrounding portion 704 and the plunger rod disk surrounding portion 720 of the shell 612 shield the syringe barrel 614. The shell 612 prevents any piercing of the syringe barrel 14 and stopper 19 and avoids any withdrawal of a drug contained inside the syringe barrel 14.

Referring to FIGS. 33-36, with the syringe barrel 614 enclosed within the shell 612, the plunger rod disk surrounding portion 720 encloses the disk 480 of the plunger rod 616 therein.

In this manner, the disk 480 enclosed within the plunger rod disk surrounding portion 720 prevents movement of the plunger rod 616 in a distal direction DD thereby preventing any leakage that should occur when high pressures are applied on the plunger rod 616 leading to sterility breakage.

The disk 480 enclosed within the plunger rod disk surrounding portion 720 prevents movement of the plunger rod 616 in a proximal direction PD and provides three different functions. First, this configuration avoids the withdrawal of the plunger rod 616 from the shell 612. Second, this configuration provides tamper evidence feature as the disk 480 of the plunger rod 616 ensures that the plunger rod 616 cannot be replaced if it has been removed. Also, the disk 480 of the plunger rod 616 guarantees the sterility of the product as it limits the displacement of the stopper 19 during transportation, e.g., the remaining bubble always present inside the container can be put under pressure during air transportation and lead to sterility loss.

Additionally, referring to FIGS. 33-36, with the syringe 613 enclosed within the shell 612, the first shell proximal aperture 708 and the second shell proximal aperture 724 have specific diameters to allow for the free rotation of the plunger rod 616 and the syringe 613. In this manner, for example, when a nurse wants to control the integrity of the product and read information present on a label affixed to a surface of the syringe barrel 14, she will be able to rotate the syringe 613 by rotating the plunger rod 616. Additionally, the syringe flange surrounding portion 704 is sized to minimize storage space but provide flange protection to the flange 40 of the syringe barrel 14 and to prevent any flange breakage.

Referring to FIGS. 34-36, the disk 480 is sized to contact the walls 722, 726 of the plunger rod disk surrounding portion 720, with the syringe barrel 14 enclosed within the shell 612, to prevent movement of the plunger rod 616 in a distal direction DD and a proximal direction PD, as described above. Also, the disk 480 is sized such that with the syringe barrel 14 removed from the shell 612, the plunger rod 616 is adapted to advance stopper 19 and plunger rod 616 is sized for movement within interior chamber 36 of syringe barrel 14, i.e., the disk 480 can slide within the syringe barrel 14.

Referring to FIGS. 33-36, packaging of a syringe 613 within shell 612 will now be described. Initially, syringe barrel 614, plunger rod 616, and shell 612 are sterilized according to techniques known to those of ordinary skill in the art. In some embodiments, syringe barrel 614 may be pre-filled as described above.

Next, a plunger rod 616 of the present disclosure can be connected to the syringe 613 via engagement of the securement feature 476 of the plunger rod 616 with the engagement portion 56 of the stopper 19 as shown in FIG. 1. Referring to FIGS. 34 and 35, the syringe 613 can be loaded within one of the shell portions 601, 602 such that the flange 40 of the syringe barrel 614 is received within the syringe flange surrounding portion 704 and the disk 480 of the plunger rod 616 is received within the plunger rod disk surrounding portion 720. Next, the first shell portion 601 and the second shell portion 602 can be engaged and moved to the closed position via the hinge 660 with the syringe 613 properly positioned within the shell 612 as shown in FIGS. 34-36.

When a user desires to remove the syringe 613 from the shell 612, a pull tab strip 497 of a clear shrink band 495 (FIGS. 38 and 39) is pulled and removed. Next, the first shell portion 601 and the second shell portion 602 can be separated and the syringe 613 removed. Advantageously, the syringe 613 is ready to be administered immediately upon removal of the shell 612.

Referring to FIGS. 38 and 39, the clear shrink band 495 includes a pre-perforated pull tab strip 497 that provides tamper evidence and is proof of the package integrity maintenance as the pull tab strip 497 needs to be pulled and removed for opening the shell 412, 612 and giving access to the pre-filled syringe 13, 413, 613. In one embodiment, the band 495 has an easy opening with two vertical pre-cut perforations with a chevron style cutting along the length of the band 495, which are also tamper evidence means.

In one embodiment, the shell 412, 612 may include a paper security label 498 that has generic wording from an existing top web.

All of the components of syringe packaging system 410, 610 may be constructed of any known material, and are desirably constructed of medical-grade polymers.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A syringe packaging system, comprising:
   a pre-filled syringe, comprising:
      a syringe barrel having a proximal end, a distal end, and a sidewall extending therebetween and defining a chamber, the proximal end having a flange;
      a fluid disposed within the chamber of the syringe barrel;
      a stopper slidably disposed within the chamber of the syringe barrel; and
      a plunger rod having a proximal end, a distal end engageable with a portion of the stopper, a proximal disk, and a distal disk; and
   a shell enclosing the syringe barrel and having a proximal end and a distal end, the proximal end including a syringe flange surrounding portion having a top wall that defines a shell proximal aperture, a bottom wall, and a sidewall extending therebetween,
   wherein with the syringe barrel enclosed within the shell, the proximal disk of the plunger rod limits movement of the plunger rod in a distal direction and the distal disk of the plunger rod limits movement of the plunger rod in a proximal direction.

2. The syringe packaging system of claim 1, wherein the top wall defines an upper surface and a lower surface.

3. The syringe packaging system of claim 2, wherein contact between the proximal disk and the upper surface of the top wall limits movement of the plunger rod in the distal direction.

4. The syringe packaging system of claim 2, wherein contact between the distal disk and the lower surface of the top wall limits movement of the plunger rod in the proximal direction.

5. The syringe packaging system of claim 1, wherein a diameter of the proximal disk is greater than a diameter of the plunger rod.

6. The syringe packaging system of claim 1, wherein a diameter of the distal disk is greater than a diameter of the plunger rod.

7. The syringe packaging system of claim 1, wherein the proximal disk is disposed between the distal disk and the proximal end, and the distal disk is disposed between the proximal disk and the distal end.

8. The syringe packaging system of claim 1, wherein the proximal disk is spaced from the distal disk.

9. The syringe packaging system of claim 1, wherein the syringe flange surrounding portion encloses the flange of the syringe barrel therein.

10. The syringe packaging system of claim 1, wherein, with the syringe barrel enclosed within the shell, a portion of the plunger rod extends from the shell proximal aperture.

11. The syringe packaging system of claim 1, wherein the proximal end of the plunger rod includes a thumb pad.

12. A syringe packaging system of claim 1, further including a label securable to a portion of the first shell portion and to a portion of the second shell portion to connect the first shell portion and the second shell portion with the syringe barrel enclosed within the first shell portion and the second shell portion.

13. A syringe packaging system of claim 1, wherein the plunger rod defines at least one notch, and wherein with the syringe barrel enclosed within the shell, the at least one notch of the plunger rod is engaged with a portion of the shell to limit movement of the plunger rod in at least one of a distal direction and a proximal direction.

14. A syringe packaging system, comprising:
   a pre-filled syringe, comprising:
      a syringe barrel having a proximal end, a distal end, and a sidewall extending therebetween and defining a chamber, the proximal end having a flange;
      a fluid disposed within the chamber of the syringe barrel;
      a stopper slidably disposed within the chamber of the syringe barrel; and a plunger rod having a proximal end and a distal end engageable with a portion of the stopper; and a shell enclosing the syringe barrel, the shell comprising:

a first shell portion having a proximal end and a distal end having a disk-shaped bottom portion; and a second shell portion having a proximal end and a distal end, wherein with the first shell portion engaged with the second shell portion to form the shell, the distal end of the first shell portion closes the distal end of the second shell portion, and wherein with the syringe barrel enclosed within the shell, the distal end of the first shell portion shields the distal end of the syringe barrel.

15. The syringe packaging system of claim 14, wherein the plunger rod includes a proximal disk and a distal disk.

16. The syringe packaging system of claim 15, wherein a diameter of the proximal disk is greater than a diameter of the plunger rod.

17. The syringe packaging system of claim 15, wherein a diameter of the distal disk is greater than a diameter of the plunger rod.

18. The syringe packaging system of claim 14, wherein with the first shell portion engaged with the second shell portion to form the shell, the proximal end of the first shell portion and the proximal end of the second shell portion together define a syringe flange surrounding portion having a top wall that defines a shell proximal aperture, a bottom wall, and a sidewall extending therebetween.

19. A syringe packaging system, comprising:

a pre-filled syringe, comprising:

a syringe barrel having a proximal end, a distal end, and a sidewall extending therebetween and defining a chamber, the proximal end having a flange;

a stopper slidably disposed within the chamber of the syringe barrel; and a plunger rod having a proximal end and a distal end engageable with a portion of the stopper; and a shell enclosing the syringe barrel, the shell comprising:

a first shell portion having a proximal end, a distal end, and a first sidewall;

a second shell portion having a proximal end, a distal end, and a second sidewall; and a hinge connected to a portion of the first shell portion and a portion of the second shell portion, the hinge connecting the first shell portion and the second shell portion together such that the shell is transitionable between an open position and a closed position in which the distal end of the syringe barrel is enclosed within the first shell portion and the second shell portion.

20. The syringe packaging system of claim 19, wherein the hinge is connected to the first sidewall of the first shell portion and the second sidewall of the second shell portion.

21. The syringe packaging system of claim 19, wherein, with the shell in the closed position, the first shell portion and the second shell portion together define a syringe flange surrounding portion having a top wall that defines a first shell proximal aperture, a bottom wall, and a sidewall extending therebetween, and wherein the syringe flange surrounding portion encloses the flange of the syringe barrel therein.

22. The syringe packaging system of claim 21, wherein the syringe flange surrounding portion is disposed adjacent the proximal end of the first shell portion and the proximal end of the second shell portion.

23. The syringe packaging system of claim 19, wherein the plunger rod includes a plunger rod disk disposed between the proximal end of the plunger rod and the distal end of the plunger rod.

24. The syringe packaging system of claim 23, wherein a diameter of the plunger rod disk is greater than a diameter of the plunger rod.

25. The syringe packaging system of claim 23, wherein, with the shell in the closed position, the first shell portion and the second shell portion together define a plunger rod disk surrounding portion having a top wall that defines a second shell proximal aperture, a bottom wall, and a sidewall extending therebetween, and wherein the plunger rod disk surrounding portion encloses the plunger rod disk therein.

26. The syringe packaging system of claim 25, wherein, with the shell in the closed position, contact between the plunger rod disk and the plunger rod disk surrounding portion limits movement of the plunger rod in a distal direction and in a proximal direction.

27. The syringe packaging system of claim 25, wherein, with the shell in the closed position, a portion of the plunger rod extends from the second shell proximal aperture.

28. The syringe packaging system of claim 19, wherein the distal end of the first shell portion includes a first bottom wall and the distal end of the second shell portion includes a second bottom wall, and wherein, with the shell in the closed position, the first bottom wall overlaps the second bottom wall.

29. The syringe packaging system of claim 28, wherein, with the shell in the closed position, the overlapping first and second bottom walls shield the distal end of the syringe barrel.

30. The syringe packaging system of claim 19, wherein one of the first shell portion and the second shell portion include a transparent window.

31. The syringe packaging system of claim 19, wherein, with the shell in the open position, a longitudinal axis of the first shell portion is parallel to a longitudinal axis of the second shell portion.

32. The syringe packaging system of claim 19, wherein the hinge is connected to a first bottom wall of the first shell portion and connected to a second bottom wall of the second shell portion.

33. The syringe packaging system of claim 32, wherein a portion of the first shell portion is pivotable between a closed position and an open position.

34. The syringe packaging system of claim 32, wherein a portion of the first shell portion is pivotable between the closed position and the open position via a second hinge.

35. The syringe packaging system of claim 32, wherein, with the shell in the open position, a longitudinal axis of the first shell portion and a longitudinal axis of the second shell portion are collinear.

* * * * *